US 8,336,403 B2

(12) United States Patent
Tajima

(10) Patent No.: US 8,336,403 B2
(45) Date of Patent: Dec. 25, 2012

(54) PIPETTE TIP HAVING CARRIER/FLUID ENCLOSED THEREIN, APPARATUS FOR TREATING PIPETTE TIP HAVING CARRIER/FLUID ENCLOSED THEREIN AND METHOD OF TREATING PIPETTE TIP HAVING CARRIER/FLUID ENCLOSED THEREIN

(75) Inventor: Hideji Tajima, Matsudo (JP)

(73) Assignee: Universal Bio Research Co., Ltd, Matsudo-Shi, Chiba (JP)

( * ) Notice: Subject to any disclaimer, the term of this patent is extended or adjusted under 35 U.S.C. 154(b) by 362 days.

(21) Appl. No.: 12/448,689

(22) PCT Filed: Jan. 21, 2008

(86) PCT No.: PCT/JP2008/050711
§ 371 (c)(1),
(2), (4) Date: Oct. 16, 2009

(87) PCT Pub. No.: WO2008/088065
PCT Pub. Date: Jul. 24, 2008

(65) Prior Publication Data
US 2010/0043575 A1    Feb. 25, 2010

(30) Foreign Application Priority Data

Jan. 19, 2007    (JP) .................................. 2007-10748

(51) Int. Cl.
*B01L 3/02*    (2006.01)
(52) U.S. Cl. .................................................. 73/864.11
(58) Field of Classification Search ............... 73/864.11, 73/864.01; 422/501; 436/178; 222/61
See application file for complete search history.

(56) References Cited

U.S. PATENT DOCUMENTS 3,215,500 A * 11/1965 Bittner .......................... 422/534

(Continued)

FOREIGN PATENT DOCUMENTS

EP    1835020 A1    9/2007

(Continued)

OTHER PUBLICATIONS

International Search Report issued Apr. 15, 2008, by the ISA/JP, in connection with International Application No. PCT/JP2008/050711 (English translation thererof included in cite no. B7, namely WO2008/088065 A1).

(Continued)

*Primary Examiner* — Peter J Macchiarolo
*Assistant Examiner* — Tamiko Bellamy
(74) *Attorney, Agent, or Firm* — Haynes and Boone, LLP

(57) ABSTRACT

The present invention relates to a pipette tip having a support and a fluid enclosed therein, an apparatus for treating the pipette tip having a support and a fluid enclosed therein, and a method of treating the pipette tip having a support and a fluid enclosed therein. The present invention aims at providing separation and purification that may be performed more efficiently and rapidly than the treatments using a conventional treatment using liquid chromatograph or a filter, and constituted to have a function for sustainedly activating the support by comprising a pipette tip comprising an attachment opening that is to be attached to a nozzle for sucking and discharging a gas or to a connecting tube attachable to the nozzle and may be communicated with the nozzle, and an opening that allows flow-in and flow-out of a liquid in response to the suction and discharging of the gas; a support enclosed in the pipette tip, which may adsorb or capture a biological material in the liquid or react with or bond to the biological material; and a fluid for sustainedly activating the support, which comprises a predetermined liquid or a predetermined gas that is enclosed in the pipette tip in a breakable state and comes into contact with the support.

12 Claims, 13 Drawing Sheets

U.S. PATENT DOCUMENTS

| | | | | |
|---|---|---|---|---|
| 5,149,425 | A | 9/1992 | Mazid | 210/198.2 |
| 5,240,601 | A | 8/1993 | Mazid | 210/198.2 |
| 5,904,663 | A | 5/1999 | Braverman et al. | 604/5.01 |
| 6,416,487 | B1 | 7/2002 | Braverman et al. | 604/5.01 |
| 7,320,259 | B2 * | 1/2008 | Jessop | 73/864.11 |
| 2002/0143283 | A1 | 10/2002 | Braverman et al. | 604/5.01 |

FOREIGN PATENT DOCUMENTS

| | | |
|---|---|---|
| JP | 08-117333 A | 5/1996 |
| JP | 2001-525200 | 12/2001 |
| JP | 2007-010748 | 1/2007 |
| WO | WO 99/06098 | 2/1999 |
| WO | WO 2006/073170 A1 | 7/2006 |
| WO | WO2008/088065 A1 | 7/2008 |

OTHER PUBLICATIONS

Written Opinion issued Apr. 15, 2008, by the ISA/JP, in connection with International Application No. PCT/JP2008/050711.

* cited by examiner

US 8,336,403 B2

PIPETTE TIP HAVING CARRIER/FLUID ENCLOSED THEREIN, APPARATUS FOR TREATING PIPETTE TIP HAVING CARRIER/FLUID ENCLOSED THEREIN AND METHOD OF TREATING PIPETTE TIP HAVING CARRIER/FLUID ENCLOSED THEREIN

CROSS REFERENCE

This application is a United States national phase application of co-pending international patent application number PCT/JP2008/050711, filed Jan. 21, 2008, which claims priority to Japanese patent application number 2007-10748, filed Jan. 19, 2007, the disclosures of which are incorporated herein by reference.

TECHNICAL FIELD

The present invention relates to a pipette tip having a support and a fluid enclosed therein, an apparatus for treating the pipette tip having a support and a fluid enclosed therein, and a method of treating the pipette tip having a support and a fluid enclosed therein.

BACKGROUND ART

Conventionally, a cylindrical container, called a column, having a liquid inlet and outlet in the center of an upper and lower circular plates, is filled with a particulate filler, called a gel, having a particle diameter of ten to several hundred microns, so that removal, separation and purification of a substance are performed utilizing the interaction between solute molecules and the gel when a liquid is made to flow from either the upper or lower liquid inlet or outlet by a pump or the like.

Incidentally, treatment steps using a column requires a large amount of transfer liquid (transfer phase) since a solution comprising a target material to be separated and purified is passed while contacting with a filler in the column in one direction. As a result, the materials included in the solution are separated into the materials to be captured by the filler and the materials to be flown out with the transfer liquid. Where a useful target material is included in the materials that are flown out, there was a problem that the target material to be separated and purified is diluted since the transfer liquid is in a large amount.

For example, where a target useful protein is separated from a residual liquid from which major proteins have been removed, as in the treatment of the proteins in the blood, there was a problem that the residual liquid is diluted since a large amount of transfer liquid is flown in the column in the treatment using a conventional column, and concentration of the residual liquid is required, and thus the treatment becomes complex.

Accordingly, the inventors of the present application have made a pipette tip comprising an attachment opening that is to be attached to a nozzle for sucking and discharging a gas or to a connecting member attachable to the nozzle, and an opening that allows flow-in and flow-out of a liquid in response to the suction and discharging of the gas to adsorb or capture the biological material in the liquid, and enclosed a support that may react with or bond to the biological material in the pipette tip, so that the direction of the flow of the liquid contacting with the support becomes bidirectional. This constitution allows separation of a target material using relatively a small amount of a liquid by repeating suction and discharging with respect to the pipette tip. The inventors have made possible to perform separation and purification more efficiently and rapidly than the treatment using a conventional column, and aimed at improving the separation performance of the target material using an easier and smaller scale structure (Patent Document 3).

However, there were problems that where air bubbles are included between gel particles during enclosing a support such as a support for affinity chromatography in a column or a pipette tip, passage of the liquid is obstructed and unreacted parts may be generated, and thus the column or pipette tip needs to be stored in the state that the air bubbles between the gel particles are completely removed.

Furthermore, there were problems that where the gel enclosed in the column or pipette tip is dried, the volume is changed, and as a result, the performance of the column may be deteriorated since the column correlates with the reaction volume, and that cracking may occur in the gel and the gel is disabled.

Moreover, even where the gel is fixed on thread or beads, there was a problem that air bubbles may not be removed after drying, and deformation or separation may occur due to drying.

In addition, although proteins, enzymes, antibodies and the like may be solid-phased in dried state and stored, those forming a subunit such as metal proteins and flavin having a solid-phase factor had a problem that they are dissociated once they are dried and may not be reconstructed.

Moreover, it was necessary to store proteins and the like in an antiseptic agent such as sodium azide so as to prevent decomposition.

Non Patent Document 1: "Liquid Chromatography Q& A" (published by Gihodo Shuppan Co., Ltd., June 2006, written by Itaru Matsushita)
Non Patent Document 2: "Reality of Liquid Chromatography" (published by Sankyo Publishing Co. Ltd., 1976, written by Akira Etoh)
Patent Document 1: WO2006/1073170

DISCLOSURE OF THE INVENTION

Problem to be Solved by the Invention

Accordingly, the first purpose of the present invention is to provide a pipette tip having a support and a fluid enclosed therein, an apparatus for treating the pipette tip having a support and a fluid enclosed therein, and a method of treating the pipette tip having a support and a fluid enclosed therein, which may improve the separation performance of the support and may perform treatments at higher reliability with respect to separation and purification of the support, by enclosing the support while preventing changes such as drying and decomposition to maintain the activation of the support.

The second purpose is to provide a pipette tip having a support and a fluid enclosed therein, an apparatus for treating the pipette tip having a support and a fluid enclosed therein, and a method of treating the pipette tip having a support and a fluid enclosed therein, which has high separation performance and high efficiency and enables treatments using a small-scale apparatus, by using a relatively small amount of the support, and a small amount of a liquid that is not diluted by a transfer liquid.

The third purpose is to provide a pipette tip having a support and a fluid enclosed therein, an apparatus for treating the pipette tip having a support and a fluid enclosed therein, and a method of treating the pipette tip having a support and a fluid enclosed therein, which may facilitate the automation of the consistent treatments using conventional columns.

The fourth purpose is to provide a pipette tip having a support and a fluid enclosed therein, an apparatus for treating the pipette tip having a support and a fluid enclosed therein, and a method of treating the pipette tip having a support and a fluid enclosed therein, which are readily handled by using smaller pressure than that in a treatment using a filter having a small pore diameter, and the like, and may decrease energy for the treatment and shorten the treatment time.

Means for Solving the Problem

The first invention is a pipette tip having a support and a fluid enclosed therein having a function for sustainedly activating the support, comprising a pipette tip comprising an attachment opening that is to be attached to a nozzle for sucking and discharging a gas or to a connecting tube attachable to the nozzle and may be communicated with the nozzle, and an opening that allows flow-in and flow-out of a liquid in response to the suction and discharging of the gas; a support enclosed in the pipette tip, which may adsorb or capture a biological material in the liquid or react with or bond to the biological material; and a fluid for sustainedly activating the support, which comprises a predetermined liquid or a predetermined gas that is enclosed in the pipette tip in a breakable state and comes into contact with the support.

As used herein, the "support" refers to an insoluble solid matter capable of adsorbing, reacting with, binding to, or capturing biological materials in fluids, which may be in any shape such as particulate, block-shape, thin film-shape, thin plate-shape, membrane-shape, plate-shape, thin rod-shape, thread-shape, rope-shape or indeterminate form. The support does not necessarily comprise one solid, but may comprise multiple solids, for example, may comprise multiple particulate supports. Furthermore, a combination of a support and a base that supports the support, for example, a thread-shaped support and a core on which the support is wound, may be used. Moreover, the size of the support varies and may be or may not be capable of passing through the opening. Examples of the support material include those made of flexible or non-flexible materials including rubber, silicone, polyethylene, polystyrene, polypropylene, urethane, cellulose or fiber materials such as nylon, as well as organic materials comprising natural materials, or inorganic materials such as glass fibers, silica, ceramics, non-magnetic or magnetic metals, metal compounds or semiconductors. Furthermore, the support includes a gel, a porous body, a permeable porous body and a water bearable matter.

For example, a block-shaped permeable porous support, i.e., a support in which a three-dimensional network skeleton and its voids are integrated may be used as the support. In the support, the skeleton size and the passage size may be independently determined, and increase in the passage size enables sucking and discharging at a lower pressure as compared with that of particulate support. However, as the percentage of voids is increased, the absorption capacity and the surface area are decreased (BIO INDUSTRY, Vol. 21, No. 11, 2004). In this case, flow-out from the opening of the pipette tip may be prevented by suitably determining the size. Therefore, the structures of the pipette tip and its interior part may be simplified without requiring an enclosing part for preventing flow-out of the support. Unlike the particulate support, the block-shaped support is not dispersed or does not move about in the liquid by flow-in and flow-out of the liquid. The "block-shape" includes columnar shape, prismatic shape, spherical shape and the like.

The support is provided with a chemical material such as a functional group or a biological material, for adsorbing, reacting with, binding to, or capturing a biological material. The biological material or chemical material is provided to the support by binding to or reacting with, or adsorbing these functional groups and the like. Examples of the biological material provided to the surface of the support include affinity ligands and affinity tags such as an antigen, an antibody, an enzyme, a substrate, a receptor, and a His-tag. Such support is referred to as a filler in liquid chromatography, which is an insoluble solid phase that is filled in a predetermined container selected to adsorb a target biological material included in a predetermined liquid, so-called as a transfer phase.

Furthermore, the support may be a support on which one or more kinds of predetermined kinds of biological materials or chemical materials are fixed or capable of fixing on the predetermined positions (for example, positions arrayed in a matrix or an array at intervals) that may be identified from outside of one support, or by each predetermined support that may be identified from outside of the multiple supports (for example, by each support where the supports are arrayed in a line by a predetermined order, by each support identified by color, or by each support identified by a luminescence material such as a fluorescent material), and the biological material or chemical material is made responsible to the position or support in advance. In this case, the presence or absence of the bond or reaction with these biological materials is measured by detecting luminescence in each fixed position in one support or in each support in multiple supports by contacting a solution comprising a biological material that has been labeled with a labeling material comprising a luminescence material such as a fluorescent material and having a possibility of bonding or the like with these biological materials, with the support in the pipette tip, whereby the structure, property, presence or absence, correlation and the like of the target biological material may be analyzed.

The "biological material" includes biopolymers or low molecular materials, for example, genetic materials such as a nucleic acid, proteins, sugars, sugar chains, peptides, and pigments. Examples of the biological material include cells, bacteria (*E. coli, staphylococcus* bacteria and the like), fungi (mold, yeast and the like), protozoa (ameba, malaria and the like), or microorganisms in biological tissues and the like, viruses and the like. The biological material may also be used as a detection material which detects the bonding of a receptor biological material that is bindable to the biological material, as a ligand, and captures, separates, and extracts the receptor biological material. As to the receptor, biological materials including genetic materials such as a nucleic acid, proteins, sugar chains, and peptides, which are bindable to the respective genetic materials such as nucleic acids, proteins, sugar chains and peptides as mentioned above, are appropriate. Moreover, the "filter" refers to a member for use in separation of a target material based on the size of the target material by setting a predetermined pore diameter.

The "adsorbing or capturing the biological material or reacting with or binding to the biological material" refers to, for example, the case where the reaction or bonding is performed by chemical adsorption by covalent bonding (for example, by functional groups such as a carboxyl group, an amino group and a hydroxy group), ion bonding, hydrophobic interaction, hydrogen bonding, coordinate bonding or the like, by physical adsorption, or electromagnetic interaction or capturing, or by the specific reaction with the bonding material fixed by the adsorption or the like on the support (reaction between various receptors and ligands, for example, an antigen and an antibody, a nucleic acid and a complementary nucleic acid, a maltose-bonded protein and maltose, IgG and Protein A and the like), or by other method. Alternatively, the support may be formed by a porous member, a convex-concave member or a fibrous member so as to improve ability of reacting or bonding with various materials comprising biological materials. In order to fix a complementary biological material to the support so as to react with or bind to a biological material, the support is designed so that a functional group may be expressed or generated. To achieve this, the functional group for use in fixing of the biological material may be expressed or generated by, for example, hydrolyzing peptide bonds of "polyamide polymer" including silk and the like, nylons (for example, 3-nylon, 6-nylon, 6,6-nylon, 6,10-nylon, 7-nylon, 12-nylon and the like) and wholly aromatic polyamides such as PPTA (polyparaphenylene terephthalamide), heterocycle-containing aromatic polymer, or the like. Examples of the functional group bindable to the biological material include a carboxyl group —COOH, an amino group —NH$_2$, or derivatives thereof. Here, the pore diameter suitable for fixing the biological material is, for example, several micrometers or less.

The "connecting tube" is a tube-like tool for use in communicatably connecting the nozzle and the pipette tip, in which one side of the tube, for example, an inner surface or one end is attachable to the nozzle and another side, for example, an outer surface or another end is attachable to the pipette tip. Where the nozzle is attached to the inner surface of the connecting tube and the pipette tip is attached to the outer surface of the connecting tube, and the perforable member is positioned inside of the pipette tip where the connecting tube is attached to the pipette tip, the perforable member is hard to contact with the outside substances. Therefore, cross-contamination due to contamination of the nozzle may be prevented.

The "pipette tip" refers to a container capable of accommodating a support, which comprises an attachment opening that is to be directly or indirectly attached to or attachable to a nozzle for sucking and discharging a gas, and an opening that allows flow-in and flow-out of a liquid in response to the suction and discharging of the gas. The shape of the pipette tip is not limited to a typical tip-form having a wide diameter tube and a narrow diameter tube. In this case, preferably, at the tip of the narrow tube is provided an opening and on the side of the wide tube is provided an attachment opening. For example, the wide tube may be in a quadratic prism-shape instead of a wide diameter tube, and the narrow tube may be a prism-shaped tube instead of a narrow diameter tube. Furthermore, the support is accommodated in, for example, a part corresponding to the narrow tube, a part corresponding to the wide tube, or a part corresponding to a transition part between the wide tube and the narrow tube. The volume of the pipette tip is preferably capable of handling a liquid of several microliters to several hundred microliters or more. Furthermore, the pipette tip may be provided, together with a support-enclosing tube (comprises a narrow tube and a wide tube) that encloses and accommodates the support, with a reservoir tube (the widest tube) that are formed wider than the support-enclosing tube and reserves the liquid introduced from the opening. In this case, the diameter of the reservoir tube is 5 mm to 10 mm, and the volume of the support enclosed tube is 300 to 500 microliters or 50 to 200 microliters and the height is, for example 7 to 15 cm. Alternatively, the diameter of the reservoir tube is 3 to 6 mm, and the volume of the support-enclosing tube is 10 to 100 microliters. The narrow tube may be provided either integrally with the wide tube or the reservoir tube, or detachably therefrom. Moreover, the wide tube itself may be provided either integrally with the reservoir tube, or detachably therefrom.

The material of the pipette tip is preferably transparent so as to enable optical observation. Examples of the material of the pipette tip include resins such as polyethylene, polypropylene, polystyrene and acrylic resins, glass, metals such as stainless steel, metal compounds, and the like. The size is, for example, one capable of accommodating a liquid of several microliters to several hundreds microliters in the narrow tube.

The "fluid for sustainedly activating the support, which comprises a predetermined liquid or a predetermined gas" refers to a liquid or gas for maintaining the function of the support itself or support inclusive of the materials hold by the support in active state during enclosing the support. For example, where the support is gel particles, passage of the liquid is obstructed and unreacted parts are generated unless air bubbles between the gel particles are completely removed. Therefore, a 20% ethanol having antiseptic effect is used in order to maintain the gel particles in a state in which the air bubbles have been completely removed, to maintain the gel in a swelled state, and to prevent occurrence of cracking of the gel, and a buffer solution is used in order to prevent the functional groups fixed on the surface of the support from deterioration. Specifically, where a biological compound such as a protein is fixed on a support, a buffer liquid having high salt concentration such as a saline for handling biological compounds, or a solution of an antiseptic agent such as sodium azide for preventing degradation of a protein and the like is suitable. Furthermore, for example, where the functional groups bonded on the support are hydrogen groups or hydroxy groups and are oxidized upon contacting with air, for example, nitrogen gas is used as the gas in order to prevent oxidation. Since the fluid for sustainedly activating the support is "enclosed in a breakable state", it may be opened and flown out of the pipette tip, unlike the support.

The second invention is the pipette tip having a support and a fluid enclosed therein, wherein the fluid for sustainedly activating the support is enclosed in a breakable state in the pipette tip by occluding the attachment opening by a perforable member or a detachable lid member or occluding by attaching the attachment opening to the connecting tube in which the perforable member being perforable by a perforation needle is provided so as to intersect the axial direction of the attachment tube, and occluding the opening by a detachable cap.

As used herein, the "perforable member" refers to a thin film-like seal provided separately from the pipette tip or connecting tube, or a thin-walled part provided integrally with them. Since the pipette tip is occluded at the attachment opening by the perforable member and occluded at the opening by the detachable cap, it may enclose the fluid for sustainedly activating the support inside itself in a breakable state. The perforable member by which the pipette tip is occluded may be perforated by a perforation needle having a sharp shape, a size that may perforate the perforable member and a rigidity that allows perforation of the perforable member.

The third invention is the pipette tip having a support and a fluid enclosed therein, wherein the pipette tip is consisting of a wide tube, a narrow tube that communicates with the wide tube, is provided to the lower side of the wide tube and is formed narrower than the wide tube, and a transition part between the wide tube and narrow tube; the attachment opening is provided to the upper side of the wide tube; and the opening is formed on the tip of the narrow tube.

The support is enclosed in the wide tube or the narrow tube. Where the support is enclosed in the wide tube, the upper side of the wide tube may be provided with a reservoir tube formed further wider than the wide tube and the liquid flown out from the opening may be reserved. By so doing, more liquid may be introduced into the upper side than the part in which the support is enclosed, and thus a larger amount of liquid than the capacity of the wide tube and narrow tube may be brought into contact with the support. In this case, the reservoir tube is preferably formed wider than the support accommodating tube. By so doing, a step or slope between the support accommodating tube and the reservoir tube and/or a step or slope between the support accommodating tube and the passage may be utilized to latch and reliably hold the support passage preventing member or the support.

Whole or a part of the wall of the pipette tip may be formed by an electroconductive member having a predetermined electric resistance. By providing the electroconductive member to the pipette tip, heat may be generated by contacting an end terminal connected to an electric source circuit provided to the outer part of the electroconductive member to apply electric current to the electroconductive member having a predetermined electric resistance. The value of the electric current is controlled based on the treatment content, by the controlling part mentioned below.

By constituting as mentioned above, the reaction temperature may be controlled by generating heat in the electroconductive member and heating or cooling the support and liquid accommodated in the pipette tip by applying electric current to the electroconductive member formed on whole or a part of the wall of the pipette tip.

In this case, since a optimum temperature raising and lowering body may be provided to each pipette tip in advance, it is not necessary to provide outside with a heating means that satisfies various conditions. Therefore, the pipette tip has general versatility and diversity. Alternatively, the temperature may be controlled by moving the temperature raising and lowering body closer to the pipette tip having a support and a fluid enclosed therein from outside of the pipette tip.

Accordingly, the temperature may be controlled while enclosing the support in the tip, various treatments including enclosing, reaction and separation may be performed all the way through. Furthermore, since the temperature is controlled while the support is enclosed, the treatment is performed efficiently and rapidly.

Furthermore, the volume of a space in which the liquid may be accommodated in the pipette tip in which the support is enclosed, is preferably about several microliters to several hundred microliters. According to this, by suppressing the volume of the space in the pipette tip formed between the surface of the enclosed support and the inner wall surface of the container to the amount (minutely small amount) of the liquid to be used for the treatment, the liquid sucked in the narrow tube may be contacted with the whole surface of the support, whereby handling with high reliability becomes possible with respect to the minutely small amount of the liquid.

As used herein, "the space capable of accommodating the liquid" generally refers to a space formed between the inner wall of the part in which the liquid is accommodated and the surface of the enclosed support in the pipette tip.

By limiting the volume in such a manner, even if a minute amount of liquid, that is, a liquid having a volume of several microliters to several hundred microliters, is sucked into the pipette tip, the liquid may be brought into a uniform and even contact with the surface of the support. This kind of minute amount is an amount of a substance that is readily extracted from a living body and handled, normally in biochemistry, particularly in the field of DNA.

The fourth invention is the pipette tip having a support and a fluid enclosed therein, wherein pipette tip is provided with an enclosing part for enclosing the support in the pipette tip, and the enclosing part is provided to an area interposed between the perforable member provided to the attachment opening or the perforable member provided to the lid member or the attached connecting tube and the cap provided to the opening, and the liquid flown in the pipette tip and the enclosed fluid for sustainedly activating the support may pass the enclosing part.

Examples of the "enclosing part" include: permeable members such as a permeable porous member and a mesh-like member provided separately from the pipette tip, through which the support may not pass but a liquid may pass; the pipette tip itself, such as the pipette tip whose wall is deformed or processed to provide the enclosing part; or a combination of a separate member and the pipette tip whose wall or the like is processed.

Examples of the modification or processing of the wall of the pipette tip may include, for example, protruding parts projecting in the direction toward inside provided to the inner wall surface, slopes tapered toward the opening, or steps that provide an extension toward the opening in the direction toward inside, so as to partition the inner wall surface of the pipette tip between the attachment opening and the opening. By the constitution, the enclosing part is provided by modifying or processing the pipette tip, and thus the support may be reliably attached to or enclosed in the pipette tip. As used herein, the "protruding parts" and "steps" may be formed so as to project or provide an extension at a constant height from the inner wall in the direction toward inside, or at a constant thickness toward the opening, or may be formed by providing difference in height or thickness. Where the height of the projection or extension of the "protruding parts" or "steps" in the direction toward inside is uniform and high, it is preferable to interpose a spacer member as an enclosing part so as to support the support. By so doing, the liquid may pass smoothly with respect to the whole support.

In addition, the enclosing part may be provided separately from the pipette tip, as a movable one, which may not pass through the opening whereas the support itself may pass through the opening, and is connected to the support. Examples of the enclosing part using the pipette tip itself include those provided with a projection or the like projecting toward the center of the tube so as to narrow the pipette tip in a contracting manner. Furthermore, another example of the enclosing part is a spacer member which is provided either separately from the pipette tip or by processing the pipette tip, for enclosing the support in a manner to avoid tight adhesion with the pipette tip to facilitate the liquid to pass smoothly through the support. The "enclose" refers to a state where the support is not discharged or flown from the opening and the attachment opening by the flow of the liquid, including cases where the support is attached to the pipette tip, or cases where the support is locked up within a part of the region in the pipette tip.

Of these enclosing parts, the "permeable porous member" does not necessarily have to be a filter which captures a certain substance by adsorption or the like, it only has to prevent the support from flown out from the opening or the attachment opening. Specifically, where the material of the enclosing part is a thin-film like or thin-plate like porous member, membrane or the like and does not have hydroscopic property, the liquid may be passed smoothly at low pressure. Furthermore, where an enclosing part is provided by processing the pipette tip, the pressure required for sucking and discharging may be reduced by enlarging the opening with a condition that the support does not flow out.

The fifth invention is the pipette tip having a support and a fluid enclosed therein, which has one or more of support passage preventing members that are provided separately from the pipette tip to partition between the opening and the attachment opening of the pipette tip so that the enclosing part becomes capable of contacting with the flow-in liquid or the enclosed fluid for sustainedly activating the support.

Here, the "support passage preventing member" is formed from a separate member from the pipette tip. The wall of the pipette tip, a combination of a separate member and a processed wall of the pipette tip, or the like may be also used. The support passage preventing member is capable of letting a liquid (and gas) pass through by, for example, having a through pore or being formed with a clearance between the member and the inner wall surface of the pipette tip, where the size or the shape of the through pore or the clearance does not allow the support to pass through. Examples thereof include members in a wheel form, a cross form, an I-form, a radial form, a mesh form, or a ring form provided to partition the narrow tube, and a permeable porous member.

In order to prevent the outflow of the support from both of the opening and the attachment opening, the number of the support passage preventing members is preferably at least two so as to sandwich the support from both sides of the opening and the attachment opening.

Here, use of the permeable porous member enables common and reliable enclosure of various supports having a greater size than the pore diameter.

The support passage preventing member is preferably thin mesh-like thin plates having little water bearing property sandwiching the top and bottom of the support since the liquid may be passed smoothly at low pressure.

By detachably providing the separate support passage preventing member, the support may be readily enclosed and taken out.

If the reservoir tube is formed wider than the support accommodating tube, the support passage preventing member may be latched and held using a slope or step between the reservoir tube and the support accommodating tube, to thereby prevent the support from entering the reservoir tube and reliably provide the support passage preventing member.

The sixth invention is the pipette tip having a support and a fluid enclosed therein, wherein the enclosing part has protruding parts projecting in the direction toward the inside, slopes tapered toward the opening, or steps projecting in the direction toward the inside toward the opening so that the inner wall surface of the pipette tip is partitioned between the attachment opening and the opening.

The seventh invention is the pipette tip having a support and a fluid enclosed therein, wherein the protruding parts, the slopes or the steps hold the support or the support passage preventing member by latching to the pipette tip.

In the enclosing part, in order to partition the inner wall surface of the pipette tip between the attachment opening and the opening, it is preferable that the inner wall surface is provided with protruding parts projected in the direction toward inside, slopes tapered toward the opening, or steps projected in the direction toward inside toward the opening, on at least two positions that are mutually apart from each other in the direction from the attachment opening to the opening, and that the support is enclosed in the pipette tip using at least one of these protruding parts, slopes or steps.

For example, where the support is a film-like porous member or a thin plate-like porous member, the support may be enclosed more reliably or may be contacted reliably with the liquid by using other enclosing parts provided separately besides the protruding parts and the like. For example, enclosing is performed by attaching a first other enclosing part, in which the upper side of the step or the like of the pipette tip to be used for enclosing the support is provided with a peripheral part provided so as to surround the center of the pipette tip by abutting on the inner wall surface of the pipette tip; a spacer member formed in a thin plate-like shape as a whole having a member projecting toward the center from the peripheral part; and the film-like support mounted thereon (where necessary, it is supported by placing a net-like member on the lower side), and a second other enclosing part, in which a tube whose side surface is contacted with the inner wall of the pipette tip, which is attached so as to fit to surround the axis line of the pipette tip, are attached on the upper side of the film-like support to the upper side of the protruding part and the like so as to sandwich the thin film-like porous member from the top and bottom. Furthermore, for example, in order to enclose multiple particulate supports, by utilizing the protruding parts and the like, two projecting parts being apart from each other are utilized, the enclosing parts or thin plate-like porous members (for example, thin plate-like meshes) for blocking the particulate supports are attached to the projecting parts, and the particulate supports are enclosed and held between the two protruding parts. By enclosing the support reliably, the liquid may be contacted with the support by not only discharging but also suction of the liquid.

As mentioned above, the pipette tip is readily handled and has diversity and general versatility since it may readily enclose the supports having various shapes by providing at least two predetermined protruding parts apart from each other along the transfer pathway of the liquid from the attachment opening to the opening. Specifically, even a film-like porous member or a thin plate-like porous member may be enclosed and attached reliably to pass the liquid smoothly, and thus even a porous member having a small pore diameter may readily pass the liquid by sucking and discharging a gas.

The eighth invention is the pipette tip having a support and a fluid enclosed therein, wherein the pipette tip is provided with the support or support passage preventing member by utilizing the steps or slopes of the transition part in the enclosing part.

The ninth invention is an apparatus for treating a pipette tip having a support and a fluid enclosed therein, comprising a nozzle head having one or multiple nozzles for sucking and discharging a gas; a sucking and discharging mechanism through which the gas is sucked or discharged via the nozzles; one or more pipette tips each having a support and a fluid enclosed therein having one or more functions for sustainedly activating a support, which are to be attached to the nozzles or connecting tubes attachable to the nozzles to communicate or to be capable of communicating with the nozzles, each of which encloses a support that may adsorb or capture a biological material in the liquid or react with or bond to the biological material and encloses a fluid for sustainedly activating the support comprising a predetermined liquid or a predetermined gas in a breakable state and comes into contact with the support; an accommodating part group provided with a tip accommodating part that accommodates or being capable of accommodating the pipette tips each having a support and a fluid enclosed therein, and a liquid accommodating part that accommodates or being capable of accommodating various liquids, and a transfer means for transferring the nozzle head relative to the accommodating part group.

It is preferable that the apparatus for treating a pipette tip having a support and a fluid enclosed therein further has a controlling part that controls the amount of suction and discharging, speed, number of times, time or position of the nozzle, based on the structures of the nozzle, the connecting tube attached to the nozzle or the pipette tip having a support and a fluid enclosed therein, and the material conditions including the kind and concentration of the material existing in the liquid, the amount of the liquid, the temperature of the liquid or the support, or the coordinate position including the accommodating position of the liquid, and the treatment content.

As used herein, the "treatment content" refers to, for example, reaction, washing, transfer, dispensation, separation, extraction, heating, cooling, clarification, measurement, mixing, dissociation, elution, agitation or the like, or a series of these treatments combined, including repetition, in accordance with a predetermined sequence or a predetermined time schedule according to the purpose of treatment. The "time" includes a duration or a timing of sucking and discharging. Setting of the duration or timing enables setting of intermittent, continuous, or noncontiguous suction and discharging.

In cases of "reaction" treatment, for example, according to the material conditions, the suction and discharging determined by the conditions, are controlled to repeat at a predetermined speed with a liquid volume of, for example, 80% of the volume of the support enclosure region in the narrow tube, in a position of a container accommodating a corresponding reagent. The number of times of the suction and discharging is also controlled based on the determination according to the material conditions. In cases of "washing" treatment, for example, according to the material conditions, the suction and discharging are controlled to be repeated for a predetermined number of times at a predetermined speed determined in accordance with the treatment, in a position of a container accommodating a washing solution. The suction and discharging are controlled according to the treatment in the same manner. Regarding the "speed", for example, when a substance to be handled is DNA, the size is smaller than that of a protein, and thus the speed needs to be increased in order to increase the chance of encounter between DNA. Moreover, the speed differs depending on the treatment contents, and is determined reasonably, for example, the speed of suction and discharging for washing or agitation is higher than the speed for reaction treatment. Furthermore, for example, with respect to a support of an adsorption type separation membrane, suction is appropriately performed at a linear flow rate (a value obtained by diving the volume flow rate by the sectional area) of about 10 to 50 cm per hour. If the support is an ultrafiltration membrane, since the flow is one-way, a control which makes a fluid pass by means of suction or pressurization, is required. On the other hand, if the support is a filler, suction of a sample solution with a tip enables the filler to float so that a suitable condition of contact between a separating agent and an object substance contained in the sample may be achieved. Moreover, in cases of separation in conventional chromatography, the volume of adsorption, so-called dynamic capacity is inversely proportional to the flow rate, and the rate of adsorption decreases. However, control of the speed of sucking and discharging may realize a volume of adsorption closer to batch adsorption.

The "structure of the pipette tip having a support and a fluid enclosed therein" includes the shape of the pipette tip, the position of a support enclosed therein, the shape, the type, and the property of the enclosed support, and the shape of the enclosing part. The determination of the operation of sucking and discharging according to the "type of the biological substance" means, for example, to achieve easier handling with less amount of liquid to be handled at a higher speed in cases of genetic substances such as DNA whose size is typically smaller than that of a protein. The reason is that, as the size is smaller, the chance of encounter typically decreases.

Preferably, the volume of the space capable of accommodating the liquid in the pipette tip enclosing the support is about several microliters to several hundred microliters. Accordingly, the liquid accommodating part provided outside of the pipette tip having a support and a fluid enclosed therein must be able to accommodate the liquid of about several microliters to several hundred microliters in a manner such that the liquid may be sucked into the narrow tube through the opening of the narrow tube.

The tenth invention is the apparatus for treating the pipette tip having a support and a fluid enclosed therein, wherein the pipette tip having a support and a fluid enclosed therein comprises a pipette tip comprising an attachment opening that is to be attached to a nozzle or to a connecting tube and may be communicated with the nozzle, and an opening that allows flow-in and flow-out of a liquid in response to the suction and discharging of the gas; a support enclosed in the pipette tip; and a fluid for sustainedly activating the support that comprises a predetermined liquid or a predetermined gas that is enclosed in the pipette tip in a breakable state and comes into contact with the support, and the fluid for sustainedly activating the support is enclosed in a breakable state in the pipette tip by occluding the attachment opening of the pipette tip having a support and a fluid enclosed therein by a perforable member or a detachable lid member, or occluding by attaching the attachment opening to the connecting tube in which a perforable member is provided so as to intersect the axial direction of the attachment tube, and occluding the opening by a detachable cap.

The eleventh invention is the apparatus for treating the pipette tip having a support and a fluid enclosed therein, wherein the nozzle head has one or multiple perforation needles for perforating the perforable member and the perforation needles are provided so as to have a number identical to the number of the one or a series of multiple nozzles provided to the nozzle head, and mutual array intervals identical to the mutual array intervals between the nozzles.

It is preferable that the axial direction of the perforation needle is provided to the nozzle head so that it runs along the vertical direction, as in the pipette tip having a support and a fluid enclosed therein. The "array" may be in the form of one line or a matrix. Furthermore, in order to transfer the perforation needle in the vertical direction, the needle is provided to the nozzle head by fixing and the nozzle head is transferred in the vertical direction by the transfer means, or a perforation needle-driving part that transfers the perforation needle with respect to the nozzle head is provided. The "array interval" is a distance between the centers of the matters to be arrayed. In the accommodating part group, tip accommodating parts and liquid accommodating parts that are arrayed at the array intervals similar to the above-mentioned array intervals are provided.

The twelfth invention is the apparatus for treating the pipette tip having a support and a fluid enclosed therein, wherein the nozzle head is provided with a tip drop off-preventing part that engages with the pipette tip having a support and a fluid enclosed therein to support the pipette tip having a support and a fluid enclosed therein and prevents the pipette tip having a support and a fluid enclosed therein from dropping off from the nozzle when the pipette tip having a support and a fluid enclosed therein provided to the nozzle head is pressurized at a predetermined pressure through the nozzle.

As used herein, the "pressurized at a predetermined pressure" means a case where high pressure is required for discharging by the sucking and discharging mechanism, for example, where the particle diameter of the support enclosed in the pipette tip having a support and a fluid enclosed therein is small, and the pore diameter of the passage preventing member used for enclosing the support is small, but the pore diameter is sufficiently higher than 100 nm.

Where engaging of the tip drop-off preventing part with the pipette tip having a support and a fluid enclosed therein is unnecessary or inconvenient, for example, where the detaching operation of the pipette tip having a support and a fluid enclosed therein by the tip detaching part is performed or the pipette tip having a support and a fluid enclosed therein is removed by a user, the operation or removal is made possible or easy by separating a member provided detachably and attachably with respect to the pipette tip having a support and a fluid enclosed therein from the pipette tip having a support and a fluid enclosed therein.

The thirteenth invention is the apparatus for treating the pipette tip having a support and a fluid enclosed therein, wherein the nozzle head is provided with a tip detaching part for detaching the pipette tip having a support and a fluid enclosed therein provided to the nozzle head from the nozzle.

As used herein, the "tip detaching part" is performed by separating the tip drop off-preventing part from the pipette tip having a support and a fluid enclosed therein so as to release the state of engaging.

The fourteenth invention is the apparatus for treating the pipette tip having a support and a fluid enclosed therein, wherein the sucking and discharging mechanism, and the tip detaching part and/or the perforation needle driving part are driven by shared use of an identical motor.

The fifteenth invention is the apparatus for treating the pipette tip having a support and a fluid enclosed therein, wherein the apparatus for treating a pipette tip having a support and a fluid enclosed therein comprises a perforation needle, a tip detaching part or a tip drop-off preventing part, and perforation operation of the perforation needle and the driving time or the driving position of the tip detaching part or the tip drop-off preventing part are controlled based on the substance condition and the treatment content.

As used herein, the "driving time" also includes driving timing.

The sixteenth invention is the apparatus for treating the pipette tip having a support and a fluid enclosed therein, wherein the apparatus for treating a pipette tip having a support and a fluid enclosed therein is provided with a magnetic part capable of applying and removing a magnetic field in the axial direction of the nozzle along the vertical direction, on the lower side of the nozzle.

The "magnetic part" may simplify the apparatus structure, suppress the increase in the size of the apparatus, and decrease the production cost thereof, by driving with a motor that is shared with the tip drop-off preventing part.

The seventeenth invention is a method of treating a pipette tip having a support and a fluid enclosed therein for one or more pipette tips having a function for sustainedly activating the support each having a support and a fluid enclosed therein comprising a pipette tip comprising an attachment opening, which are to be attached to one or more nozzles for sucking and discharging a gas or to connecting tubes attachable to the nozzles and communicated with or may be communicated with the nozzles, and an opening that allows flow-in and flow-out of a liquid in response to the suction and discharging of the gas; a support enclosed in the pipette tip, which may adsorb or capture a biological material in the liquid or react with or bond to the biological material; and a fluid for sustainedly activating the support that comprises a predetermined liquid or a predetermined gas that is enclosed in the pipette tip in a breakable state and comes into contact with the support, wherein the method comprises a step of attaching the attachment opening or the connecting tube attached to the attachment opening to the nozzle, and a step of contacting, in which the attached pipette tip having a support and a fluid enclosed therein is transferred to a predetermined liquid accommodating part and the liquid accommodated in the liquid accommodating part is contacted with the support by suction or discharging of the liquid so that the support adsorbs or captures the biological material in the liquid or reacts with or bonds to the biological material.

In the step for contacting, it is preferable to control the operations of sucking and discharging, the amounts of sucking and discharging, speed, number of times, time or position, based on the structures of the nozzle, the connecting tube attached to the nozzle or the pipette tip having a support and a fluid enclosed therein, the material conditions including the kind of the biological material existing in the liquid, the concentration, the amount of the liquid, the temperature of the liquid or the support, or the coordinate position including the accommodating position of the liquid, and the treatment content.

The eighteenth invention is the method of treating the pipette tip having a support and a fluid enclosed therein, wherein the step of attaching comprises a step of putting the fluid for sustainedly activating the support into a broken state with respect to the pipette tip having a support and a fluid enclosed therein.

Where the pipette tip having a support and a fluid enclosed therein wherein the attachment opening is covered by a thin-walled part being perforable using a predetermined perforation needle or a detachable lid member, or occluded by attaching the attachment opening to the connecting tube in which the thin-walled part being perforable using the perforation needle is provided so as to intersect the axial direction of the attachment tube, and the opening is occluded by a detachable cap, is used, the "putting into a broken state", is performed, for example, by perforating using the perforation needle or removing the lid member, attaching the attachment opening or the connecting tube of the pipette tip having a support and a fluid enclosed therein to the nozzle, and removing the cap. After the pipette tip having a support and a fluid enclosed therein is attached to the nozzle, squirt of the fluid for sustainedly activating the support in the inner part may be prevented by applying a negative pressure to the inside of the pipette tip having a support and a fluid enclosed therein during removal of the pipette tip. Furthermore, drop off of the pipette tip having a support and a fluid enclosed therein during removal of the cap may be prevented by applying the tip drop-off preventing part.

The nineteenth invention is the method of treating the pipette tip having a support and a fluid enclosed therein, which further comprises a step of dissociating in which the material bonded to the support is dissociated from the support.

The twentieth invention is the method of treating the pipette tip having a support and a fluid enclosed therein, which further comprises a step of attaching a pipette tip to the nozzle after the pipette tip having a support and a fluid enclosed therein is detached from the nozzle, or before the pipette tip having a support and a fluid enclosed therein is attached to the nozzle; a step of dispensing a liquid in which magnetic particles are suspended; and a step of applying magnetic field into the pipette tip from outside so that the magnetic particles are adsorbed on the inner wall of the pipette tip.

Here, the support is not enclosed in the above-mentioned pipette tip.

Effect of the Invention

According to the first invention, the ninth invention or the seventeenth invention, the pipette tip having a support and a fluid enclosed therein in which the support and the fluid for sustainedly activating the support to be contacted with the support are enclosed in the pipette tip in advance is used by directly or indirectly attaching the pipette tip to the nozzle through which the gas is sucked or discharged by a specific control.

Therefore, the support whose activation is maintained may initiate the treatment immediately. Furthermore, since the fluid for sustainedly activating the support is enclosed in a breakable state in advance by occluding the attachment opening and the opening of the pipette tip, even gel particles are used as the support, the state in which air bubbles between the gel particles are completely removed in advance is maintained, and the liquid is smoothly passed between the gel particles, whereby the reaction efficiency may be improved. Moreover, drying of the support such as a gel is prevented, whereby deterioration of the performance of the support and the deformation or damage of the support may be prevented.

Since the flow of the liquid is not unidirectional but may be bidirectional where the amount or the surface area contacting with the liquid of the support is constant, the liquid may be contacted with the support more efficiently by repeating suction and discharging. Therefore, separation, extraction, purification performance and treatment efficiency with respect to the support may be improved.

Furthermore, the support may be contacted with the liquid by selecting any liquid existing outside and sucking it while the support is enclosed in the pipette tip. Therefore, by replacing the treatment of the support with the controls of the relative transfer between the pipette tip having a support and a fluid enclosed therein and the container provided outside, and of sucking and discharging, the treatment may be automated, diversified and made versatile.

Since the contact efficiency between the support and the liquid may be improved by using the pipette tip having a support and a fluid enclosed therein in which the support is enclosed and the sucking and discharging mechanism having the nozzles, the necessary amount of the liquid and the necessary amount of the support may be decreased and the scale of the apparatus as a whole may be suppressed. Therefore, the same efficiency as the conventional support may be obtained by using the support by a lower amount than the amount of the conventional support.

Moreover, according to the present invention, removal, reaction, washing, temperature control, separation, stirring, dispensing, clarifying, isolation, elution and extraction may be performed by only flowing-in and flowing-out the liquid and transferring the pipette tip while the support such as a filler is kept enclosed in the pipette tip. Therefore, the treatment may be performed efficiently, rapidly and readily.

In addition, since the present invention may be applied to various treatments by selecting the speed of flowing-in and flowing-out of the liquid according to the purpose of the treatment, the pipette tip suitable for the amount of the liquid to be handled, the amount of the support, the amount of the liquid and the like, it has general versatility and diversity.

Furthermore, according to the present invention, the treatment may be performed by using an identical nozzle by detaching and attaching the pipette tip having a support and a fluid enclosed therein or other pipette tip with respect to the nozzle or the like, by using the pipette tip having a support and a fluid enclosed therein in which the support is enclosed, which is attached to the nozzle or the tip or the like attached to the nozzle. Therefore, various treatments may be performed efficiently and rapidly.

According to the second invention, the tenth invention or the eighteenth invention, the liquid from outside may be contacted with the support rapidly and reliably by putting the fluid for sustainedly activating the support into the broken state upon attachment. Furthermore, since the attachment opening of the pipette tip is occluded by the perforable member or the detachable lid member and the opening is occluded by the detachable cap, the liquid from outside may be readily contacted with the support enclosed in the pipette tip, whereby the operation of enclosing the support in an optimal state may be omitted so as to use the pipette tip having a support and a fluid enclosed therein more readily and rapidly.

According to the third invention, the pipette tip comprises the wide tube and the narrow tube formed narrower than the wide tube. Therefore, the pipette tip has general versatility since it may be applied to various containers or various amounts of the liquid. Furthermore, the support may be enclosed reliably by latching the support and the support passage preventing member by utilizing the transition part between the support accommodating tube and the flow path.

According to the fourth invention, since the support is enclosed in the pipette tip by providing the enclosing part to the area interposed between the perforable member or the lid member or the perforable member provided to the attached connecting tube and the cap provided to the opening, the liquid or gas may be flown-in and flown-out through the opening after attaching to the nozzle, whereas the support is not flown-out through the opening or the nozzle. Therefore, the perforable member or the lid member or the like may be reliably removed and the treatment may be performed smoothly.

According to the fifth invention, the support passage preventing member is provided separately from the pipette tip. Therefore, the support may be enclosed readily. Furthermore, where the support passage preventing member is attached detachably, the tip-like member may be recycled, or the material adsorbed on the support may be directly extracted or collected.

According to the sixth invention, the protruding parts, the slopes or the steps formed by protruding the wall surface of the pipette tip are provided as the enclosing parts. Therefore, the number of the parts may be decreased to decrease the production cost, and the support may be enclosed reliably.

According to the seventh invention, the support or the support passage prevention member is supported by the protruding parts, the slopes or the steps. Therefore, the support is hold by the pipette tip, and thus enclosing may be performed reliably.

According to the eighth invention, the support or support passage preventing member is hold on the pipette tip by utilizing the step or slope of the transition part from the narrow tube to the wide tube of the pipette tip. Therefore, the support may be hold readily and reliably by latching without specific processing of the pipette tip.

According to the ninth invention or the seventeenth invention, the pipette tip having a support and a fluid enclosed therein in which the support is enclosed in the pipette tip is attached to a member used for a sucking and discharging mechanism such as a nozzle or a tip attached to the nozzle or the like, and the amount, speed, number of times or position of the suction and discharging with respect to the nozzle may be controlled based on the structure or the like of the pipette tip.

Therefore, according to the present invention, by using a pipette tip having a support and a fluid enclosed therein having a predetermined structure and carefully controlling the suction and discharging, the treatments such as reaction, stirring and washing between the support enclosed in the tip and the solution comprising a predetermined biological material may be performed readily, all the way through, and rapidly and efficiently with high reliability. Furthermore, the present invention has general versatility and diversity since it may handle various treatments by changing the content of the control.

According to the eleventh invention, the invention has one or multiple perforation needles for perforating the perforable members, and the pipette tips each having a support and a fluid enclosed therein may be perforated concurrently and automatically by using a perforation needle driving means that transfers the transfer means of the nozzle heads or the perforation needles with respect to the nozzle heads. Therefore, a treatment may be performed with high reliability by attaching the pipette tip having a support and a fluid enclosed therein to the nozzle rapidly and reliably without using human hands, and by contacting the liquid with the support by using the sucking and discharging mechanism.

According to the twelfth invention, where the pipette tip having a support and a fluid enclosed therein is pressurized at a predetermined pressure through the nozzle, the tip drop off-preventing part engages with the pipette tip having a support and a fluid enclosed therein to support pipette tip having a support and a fluid enclosed therein and prevents the pipette tip having a support and a fluid enclosed therein from dropping-off from the nozzle. Therefore, even a support having a small pore diameter that is enclosed in the pipette tip having a support and a fluid enclosed therein is provided so as to partition the pipette tip having a support and a fluid enclosed therein in the axial direction, the liquid may be passed. Accordingly, an ultrafiltration membrane or a microfiltration membrane may be adopted to the support, and thus the pipette tip may be used for the treatment or the like of proteins and has general versatility.

According to the thirteenth invention, by providing a tip detaching part for detaching the pipette tip having a support and a fluid enclosed therein from the nozzle, the pipette tip having a support and a fluid enclosed therein may be detached without touching the nozzle head by human hands, whereby cross-contamination may be prevented reliably, and the treatment of the pipette tip having a support and a fluid enclosed therein may be automatically performed all the way through.

According to the fourteenth invention, the sucking and discharging mechanism and the tip detaching part and/or the perforation needle driving part are driven by an identical motor. Therefore, the number of the parts may be decreased, the scale of the apparatus may be decreased and the apparatus may be produced at a low cost.

According to the fifteenth invention, by controlling the perforation operation of the perforation needle, the tip detaching part or the tip drop-off preventing part based on the material condition and the treatment content, a series of treatments may be automated continuously.

According to the sixteenth invention, the tip-like nozzle is attached to the nozzle of the apparatus for treating the pipette tip having a support and a fluid enclosed therein, and a magnetic field may be applied to the magnetic particles introduced in the pipette tip. Therefore, a series of treatments may be automated continuously by using one apparatus for treating the pipette tip having a support and a fluid enclosed therein, and combining various treatments such as separation, extraction, re-suspension and transfer of the target material captured by the magnetic particles.

According to the nineteenth invention, by separating the material having reacted with or bonded to the support enclosed in the pipette tip having a support and a fluid enclosed therein from the support, the material may be collected, recycled and analyzed conveniently.

According to the twentieth invention, by using an identical or partially identical pipette tip as the pipette tip used for the pipette tip having a support and a fluid enclosed therein, the nozzle may be shared with the pipette tip having a support and a fluid enclosed therein. Therefore, since the treatment by the pipette tip having a support and a fluid enclosed therein and the separation treatment using the pipette tip may be continuously performed all the way through, the treatment may be performed rapidly, become diverse and be automated. Furthermore, by combining the treatment by a non-magnetic support and the treatment by a magnetic support, various treatment may be performed.

BEST MODE FOR CARRYING OUT THE INVENTION

Next, the embodiments of the present invention are explained based on the drawings. Unless otherwise indicated, the explanation of the embodiments should not be construed to limit the present invention.

Figure 1:
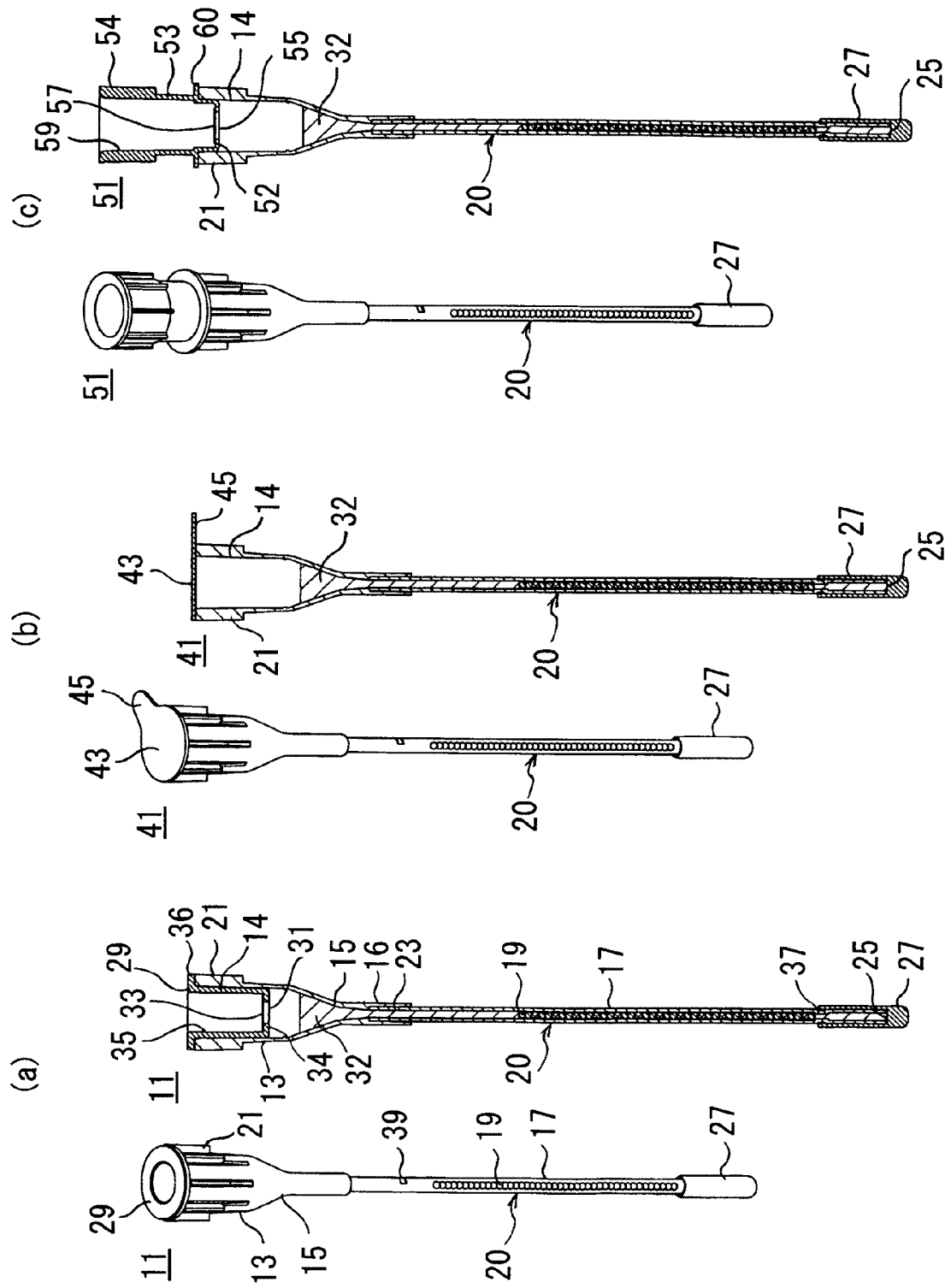
FIG. 1 is a drawing showing a pipette tip having a support and a fluid enclosed therein according to a first embodiment of the present invention.

FIGS. 1 (a), (b) and (c) are drawings showing the three kinds of the pipette tips each having a support and a fluid enclosed therein 11,41 and 51 according to the first embodiment of the present invention. In each of the pipette tips each having a support and a fluid enclosed therein 11,41 and 51, multiple particles 19 (in these cases, 43 particles) are enclosed in the pipette tip 20 as particulate supports.

Each particle 19 is labeled so as to be identified from outside by the order of alignment in an array, by various colors, or by a combination of a luminescence material or multiple luminescence materials such as various fluorescent materials and the amount ratio thereof, and each particle 19 is related to various biological materials or chemical materials fixed on the particle 19 in advance. Therefore, by identifying the particle 19 in which luminescence of the labeling material is generated by the reaction with or bond to the target biological material or the target chemical material that is labeled identifiably by other labeling material comprising a luminescence material such as a fluorescent material that is identifiable and different from the labeling material and capable of binding with the biological material or the chemical material, the corresponding fixed biological material or chemical material may be specified from the order or color of the particles 19, or the kind and amount of the labeling material such as the luminescence material.

The pipette tip 20 has the approximately cylindrical wide diameter tube 13, the approximately cylindrical narrow diameter tube 17 that communicates with the wide diameter tube 13, is formed narrower than the wide diameter tube 13 and accommodates the particles 19 therein, and the approximately funnel-shaped transition part 15 formed on the lower part of the wide diameter tube 13 and between the wide diameter tube 13 and the narrow diameter tube 17.

The narrow diameter tube 17 is fitted and attached to the lower end part 16 of the transition part 15 at its upper end part 23. It is preferable that the particulate supports are enclosed in the narrow diameter tube 17 and thereafter fixed by, for example, an adhesive, ultrasonic melt adhesion, heat melt adhesion or the like. Here, the particles 19 may adsorb or capture the biological material in the liquid introduced into the pipette tips each having a support and a fluid enclosed therein 11,41 and 51, or may react with or bond to the biological material.

To the upper side of the wide diameter tube 13 is provided with the attachment opening 14 that has a cylindrical inner wall surface to be attached to a nozzle (not depicted) through which the gas is sucked or discharged, or to be attached to the connecting tube 29 or 53 that is attachable to the nozzle. FIGS. 1 (a) and (c) each shows the case where the cylindrical inner wall surface is attached to the connecting tube 29 or 53, and FIG. 1 (b) shows the case where the cylindrical inner wall surface is directly attached to the nozzle.

To the tip of the narrow diameter tube 17 is provided with the opening 25 through which the liquid may be flown-in and flown-out by sucking and discharging the gas with the nozzle. In the narrow diameter tube 17, the particles 19 are accommodated in a linear fashion. The particle diameter of each particle 19 is, for example, about several ten micrometers to several millimeters, and the inner diameter of the narrow diameter tube 17 is formed slightly larger than the particle diameter. The inner wall surface of the lower and upper sides of the narrow diameter tube 17 in which the particles 19 are accommodated are provided with the two protruding parts 39 and 37 as the enclosing parts, which are vertically apart from each other and protruding toward inside so as to partition the inner wall surface of the pipette tip 20 between the attachment opening and the opening 25, and the multiple particles 19 are wedged and enclosed between the protruding parts. The protruding parts 39 and 37 are protruded by depressing the opposed wall surfaces of the narrow diameter tube 17 from outside in the radius direction of the narrow diameter tube 17. In so doing, the direction of depression of the protruding part 39 and that of the protruding part 37 make an angle of 90° each other.

In each pipette tip 20, the opening 25 on the tip of the narrow diameter tube 17 is occluded by the detachable cap 27. On the other hand, with regard to the attachment opening 14, as shown in FIGS. 1 (a), (b) and (c), the fashion of occlusion is different between the pipette tips each having a support and a fluid enclosed therein 11,41 and 51. As used herein, the symbols 21 are multiple protrusions formed on the upper part of the pipette tip 20 along the axial direction. They are parts for supporting the pipette tip each having a support and a fluid enclosed therein 11, 41 and 51 by engaging with the dropping-off preventing member so as to prevent the pipette tip 20 from dropping off from the nozzle during pressurizing mentioned below.

In the pipette tip having a support and a fluid enclosed therein 11, as shown in FIG. 1 (a), the attachment opening 14 of the wide diameter tube 13 is occluded by the connecting tube 29 in which the pore 31 covered by sealing from the upper side by the seal 33 as a perforable member capable of being perforated by the perforation needle 155 mentioned below is provided to the center of the bottom wall surface 34. To the upper end of the connecting tube 29 is provided with the ring-shaped flange 36 projecting in the radius direction, which abuts to the upper end of the pipette tip 20 where the connecting tube 29 is inserted to the attachment opening 14. The fluid for sustainedly activating the support 32 as the fluid for sustainedly activating the support is enclosed in the area interposed by the cap 27 and the seal 33 in a breakable state with respect to the cap 27 and the seal 33.

For the pipette tip having a support and a fluid enclosed therein 41, as shown in FIG. 1 (b), the attachment opening 14 of the wide diameter tube 13 is occluded by covering with the seal 43 as a perforable member that may be perforated by the perforation needle 155 mentioned below or peeled by hand. The seal 43 has the holding part 45 extending in the radius direction from the circular part that covers the attachment opening 14 so that the seal 43 may be gripped where it is peeled manually. The fluid for sustainedly activating the support 32 is enclosed in the area interposed by the cap 27 and the seal 43 in a breakable state with respect to the cap 27 and the seal 43.

For the pipette tip having a support and a fluid enclosed therein 51, as shown in FIG. 1 (c), the attachment opening 14 of the wide diameter tube 13 is occluded by the connecting tube 53 in which the pore 55 is provided to the center of the bottom wall surface 52, wherein the pore 55 is covered by sealing from above by the seal 57 as a perforable member that may be perforated by the perforation needle 155 mentioned below. To the side surface of the connecting tube 53 is provided with the ring-shaped guard 60 projecting in the radius direction, which abuts to the upper end of the pipette tip 20 where the connecting tube 53 is inserted in the attachment opening 14. The fluid for sustainedly activating the support 32 is enclosed in the area interposed by the cap 27 and the seal 57 in a breakable state with respect to the cap 27 and the seal 57. The symbol 54 shows multiple protrusions formed on the upper side of the outer surface of the connecting tube 53 along the axial direction.

Figure 2:
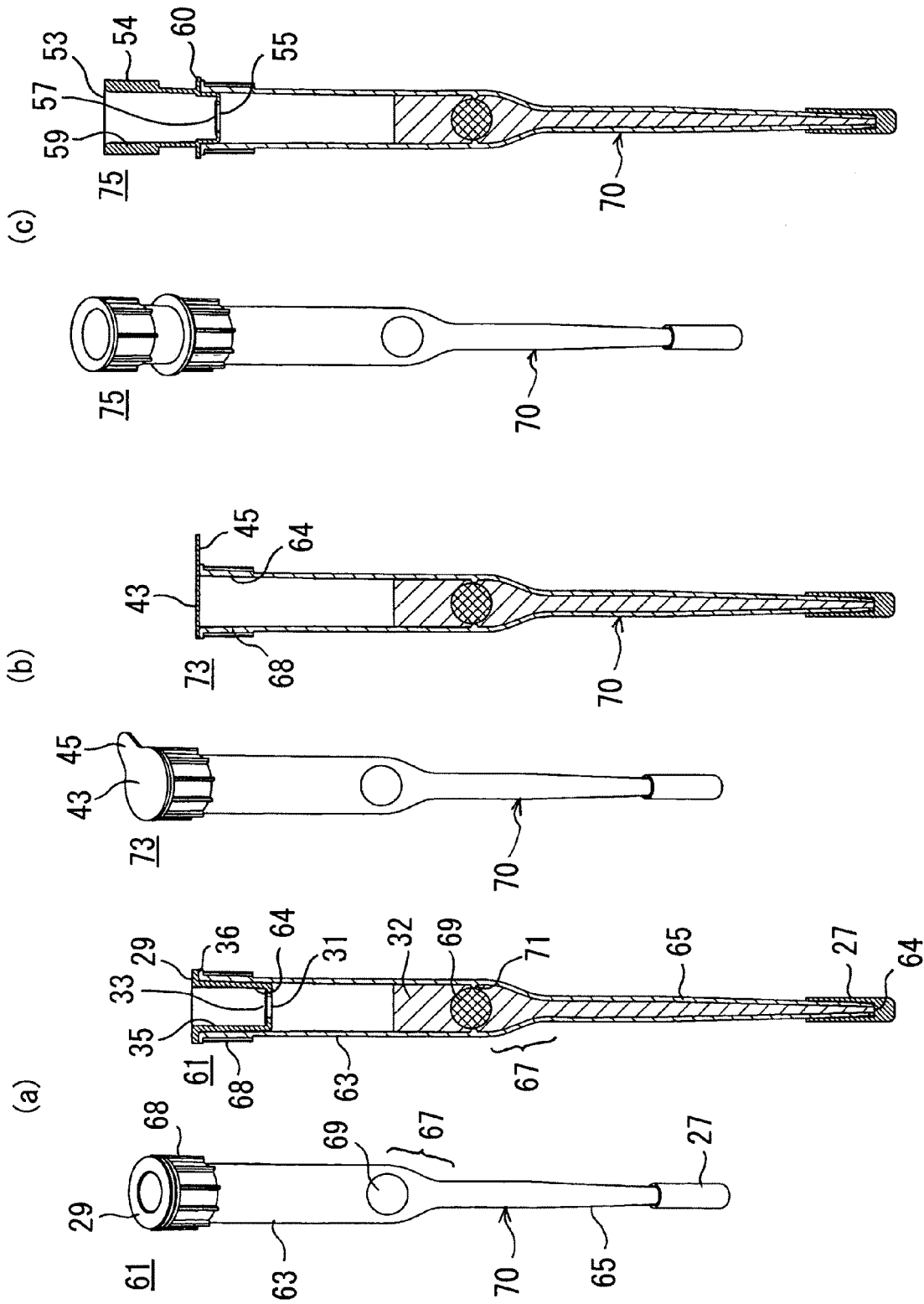
FIG. 2 is a drawing showing a pipette tip having a support and a fluid enclosed therein according to a second embodiment of the present invention.

FIG. 2 is a drawing showing the three kinds of the pipette tips each having a support and a fluid enclosed therein 61, 73 and 75 according to a second embodiment of the present invention. The symbols similar to that of FIG. 1 show similar parts, and thus the explanation thereof is not repeated here.

As shown in FIG. 2, in the pipette tips each having a support and a fluid enclosed therein 61, 73 and 75, one spherical block-shaped support 69 is enclosed in the pipette tip 70 as the support. The pipette tip 70 has the approximately cylindrical wide diameter tube 63 in which the block-shaped support 69 is enclosed, the approximately cylindrical narrow diameter tube 65 that communicates with the wide diameter tube 63 and formed narrower than the wide diameter tube 63, and the approximately funnel-shaped transition part 67 formed between the wide diameter tube 63 and the narrow diameter tube 65. The symbol 68 shows multiple protrusions provided to the upper part of the pipette tip 70 in the axial direction, which are used for supporting the pipette tips each having a support and a fluid enclosed therein 61, 73 and 75 attached to the nozzle by engaging with the horizontal engaging plate and the rotating engaging plate of the dropping-off preventing member mentioned below during pressurizing so as to prevent dropping off from the nozzle.

To the upper side of the wide diameter tube 63 is provided with the attachment opening 62 having a cylindrical inner wall surface to be attached to a nozzle (not depicted) through which the gas is sucked or discharged, or to be attached to the connecting tube 29 or 53 that is attachable to the nozzle. FIGS. 2 (*a*) and (*c*) each shows the case where the attachment opening is attached to the connecting tube 29 or 53, and FIG. 2 (*b*) shows the case where the attachment opening is directly attached to the nozzle. The wide diameter tube 63 accommodates one block-shaped support 69. The diameter of the block-shaped support 69 is, for example, several millimeters to several ten millimeters, and the inner diameter of the wide diameter tube 63 is formed slightly larger than the diameter of the block-shaped support 69. To the wide diameter tube 63 in which the block-shaped support 69 is accommodated are provided with the protruding parts 71, as the enclosing parts, at multiple positions, for example, 2 to 8 positions on the inner wall surface at intervals along the circumference direction so as to project in the direction toward inside to hold the block-shaped support 69.

In each pipette tip 70, the opening 64 provided to the tip of the narrow diameter tube 65 is occluded by the detachable cap 27. On the other hand, with regard to the attachment opening 62, there are three kinds of the pipette tips each having a support and a fluid enclosed therein 61, 73 and 75, including the case where the pipette tips each having a support and a fluid enclosed therein 61 and 75 are each attached to the nozzle via the connecting tube 29 or 53 as shown in FIGS. 2 (*a*) and (*c*), and the case where the pipette tip having a support and a fluid enclosed therein 73 is directly attached to the nozzle as shown in FIG. 2 (*b*). In the pipette tips each having a support and a fluid enclosed therein 61, 73 and 75, the cap 27 used for enclosing the fluid for sustainedly activating the support 32, the connecting tubes 29 and 53 to be provided to the attachment opening 62, and the seal 43 are similar to those provided to the pipette tip 20 as explained in the first embodiment, and thus the explanation thereof is not repeated here.

Figure 3:
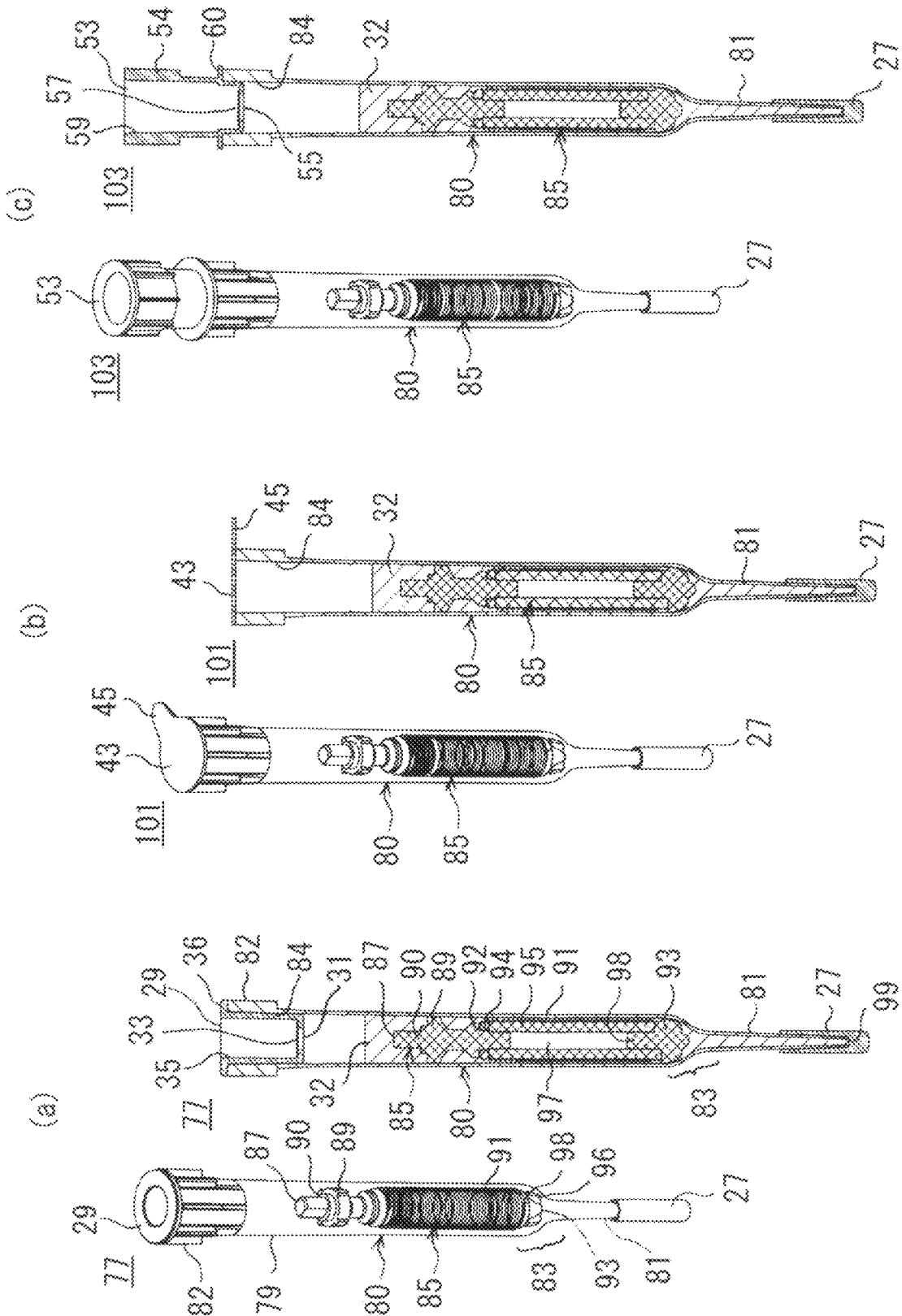
FIG. 3 is a drawing showing a pipette tip having a support and a fluid enclosed therein according to a third embodiment of the present invention.

Next, FIG. 3 is a drawing showing the three kinds of the pipette tips each having a support and a fluid enclosed therein 77, 101 and 103 according to a third embodiment of the present invention. The symbols similar to that of FIGS. 1 and 2 show similar parts, and thus the explanation thereof are not repeated here.

As shown in FIG. 3, in the pipette tips each having a support and a fluid enclosed therein 77, 101 and 103, the wound body 85 in which one rope-like support 91 as a support is wound around the cylindrical core 95 as a substrate is enclosed in the pipette tip 80. The pipette tip 80 has the approximately cylindrical wide diameter tube 79 in which the wound body 85 is enclosed, the approximately cylindrical narrow diameter tube 81 that communicates with the wide diameter tube 79 and formed narrower than the wide diameter tube 79, and the approximately funnel-shaped transition part 83 formed between the wide diameter tube 79 and the narrow diameter tube 81. The symbols 82 are multiple protrusions formed on the upper part of the pipette tip 80 along the axial direction, which are used for supporting the pipette tips each having a support and a fluid enclosed therein 77, 101 and 103 by engaging with the horizontal engaging plate and the rotating engaging plate of the dropping-off preventing part mentioned below so as to prevent dropping off from the nozzle.

To the upper side of the wide diameter tube 79 is provided the attachment opening 84 that has a cylindrical inner wall surface to be attached to a nozzle (not depicted) through which the gas is sucked or discharged, or to be attached to the connecting tube 29 or 53 that is attachable to the nozzle. FIGS. 3 (*a*) and (*c*) each shows the case where the attachment opening is attached to the connecting tube 29 or 53, and FIG. 3 (*b*) shows the case where the attachment opening is directly attached to the nozzle.

To the tip of the narrow diameter tube 81 is provided with the opening 99 through which the liquid may be flown in and flown out by sucking and discharging the gas with the nozzle, and the opening 99 is occluded by the detachable cap 27. On the other hand, with regard to the attachment opening 84, the pipette tip is attached to the nozzle via the connecting tube 29 or 53, or directly attached to the nozzle. Here, the three kinds of the pipette tips each having a support and a fluid enclosed therein 77, 101 and 103 are shown in FIGS. 3 (*a*), (*b*) and (*c*).

The wound body 85 is provided with the cylindrical core 95 in which the rope-like support 91 is wound on the side surface so as to surround the axis line. The upper end of the core 95 is provided with the passage preventing members 87 and 93 as the enclosing parts that are provided separately from the pipette tip so as to partition between the opening 99 and the attachment opening 84 of the pipette tip 80 so that the support may contact with the flown-in liquid or the enclosed fluid for sustainedly activating the support.

The passage preventing member 87 has the rod-shaped member 90 whose lower part may be set in the hollow part 97 of the core 95; the ring-shaped tiered part having teeth 89 on which multiple teeth are provided at intervals, wherein the teeth project in the radius direction of the rod-shaped member 90 and abut on the inner wall of the wide diameter tube 79; and the ring-shaped tiered part 92, which is provided to the lower side of the ring-shaped tiered part having teeth 89 and has a height that does not abut on the inner wall surface. The lower part of the passage preventing member 87 is set in the hollow part 97 by intervening the O-ring 94 between the ring-shaped tiered part 92 and the upper end of the core 95.

The passage preventing member 93 has the rod-shaped member 93 whose upper part may be set in the hollow part 97 of the core 95, and the multiple convex parts 96 provided at intervals, which are abutting to the inner wall surface of the pipette tip 80 in the radius direction in the lower part of the rod-shaped member 93. Furthermore, the upper end of the convex part 96 abuts on the lower end of the core 95, and the wound state of the rope-like support 91 is maintained by slipping the tip of the rope-like support 91 in between the upper end of the convex part 96 and the lower end of the core 95.

In each pipette tip 80, the opening 99 provided to the tip of the narrow diameter tube 81 is occluded by the detachable cap 27. On the other hand, with regard to the attachment opening 84, there are three kinds of the pipette tips each having a support and a fluid enclosed therein 77, 101 and 103, including the case where the pipette tip each having a support and a fluid enclosed therein 77 and 103 are each attached to the nozzle via the connecting tube 29 or 53 as shown in FIGS. 3 (a) and (c), and the case where the pipette tip having a support and a fluid enclosed therein 101 is directly attached to the nozzle as shown in FIG. 3 (b). In the pipette tips each having a support and a fluid enclosed therein 77, 101 and 103, the cap 27 used for enclosing the fluid for sustainedly activating the support 32, the connecting tubes 29 and 53 to be provided to the attachment opening 84, and the seal 43 are similar to those provided to the pipette tips 20 and 70 as explained in the first and second embodiments, and thus the explanation thereof is not repeated here.

Figure 4:
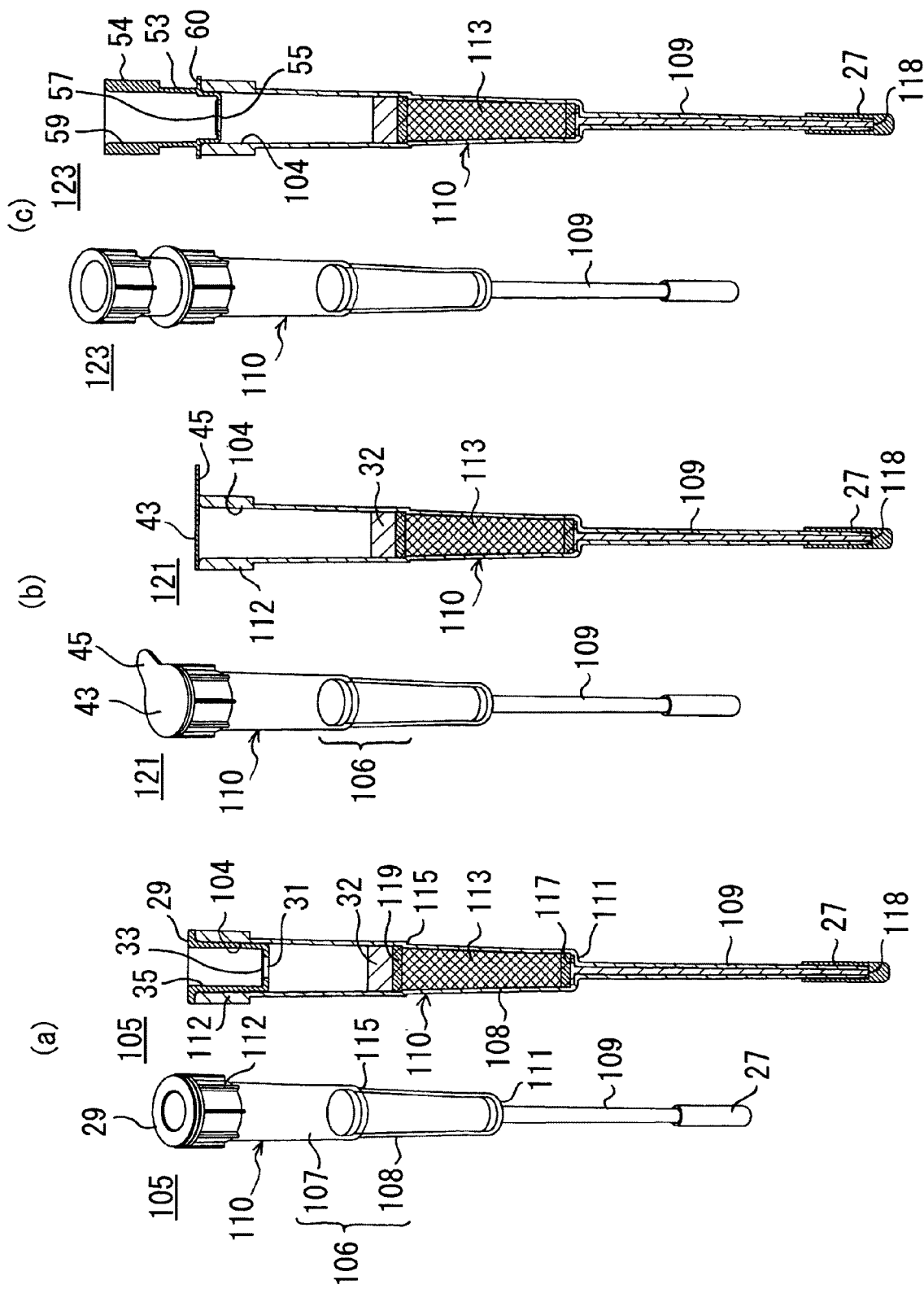
FIG. 4 is a drawing showing a pipette tip having a support and a fluid enclosed therein according to a fourth embodiment of the present invention.

FIG. 4 is a drawing showing the three kinds of the pipette tips each having a support and a fluid enclosed therein 105, 121 and 123 according to a fourth embodiment of the present invention. The symbols similar to that of FIGS. 1, 2 and 3 show similar parts, and thus the explanation thereof is not repeated here.

As shown in FIG. 4, in the pipette tips each having a support and a fluid enclosed therein 105, 121 and 123, the cylindrical block-shaped support 113 is enclosed in the pipette tip 110 as a support. The pipette tip 110 has the approximately cylindrical wide diameter tube 106 in which the cylindrical block-shaped support 113 is enclosed, the approximately cylindrical narrow diameter tube 109 formed narrower than the wide diameter tube 106, and the step-like transition part 111 formed between the wide diameter tube 106 and the narrow diameter tube 109. The wide diameter tube 106 has the support accommodating tube 108 in which the cylindrical block-shaped support 113 is accommodated, which is provided to the lower side of the wide diameter tube 106; the reservoir tube 107 capable of reserving the liquid, which is provided to the upper side of the wide diameter tube 106 and formed wider than the support accommodating tube 108; and the step 115 formed between the support accommodating tube 108 and the reservoir tube 107. The symbols 112 are multiple protrusions provided to the upper part of the pipette tip 110 in the axial direction, which are used for supporting the pipette tips each having a support and a fluid enclosed therein 105, 121 and 123 by engaging with the dropping-off preventing member mentioned below so as to prevent dropping off from the nozzle.

To the upper side of the wide diameter tube 106, namely, the upper side of the support accommodating tube 108, is provided with the attachment opening 104 having a cylindrical inner wall surface to be attached to a nozzle (not depicted) by which the gas is sucked or discharged, or to be attached to the connecting tube 29 or 53 that is attachable to the nozzle. FIGS. 4 (a) and (c) each shows the case where the attachment opening is attached to the connecting tube 29 or 53, and FIG. 4 (b) shows the case where the attachment opening is directly attached to the nozzle.

To the tip of the narrow diameter tube 109 is provided with the opening 118 through which the liquid may be flown in and flown out by sucking and discharging the gas with the nozzle, and the opening 118 is occluded by the detachable cap 27. On the other hand, with regard to the attachment opening 104, the pipette tip is attached to the nozzle via the connecting tube 29 or 53, or directly attached to the nozzle. Here, the three kinds of the pipette tips each having a support and a fluid enclosed therein 105, 121 and 123 are shown in FIGS. 4 (a), (b) and (c).

As the enclosing part, the support accommodating tube 108 that accommodates the cylindrical block-shaped support 113 holds the disc-like porous member 117 through which the liquid may pass, at the lower bottom, by latching the disc-like porous member 117 to the step of the transition part 111, and holds the disc-like porous member 119 through which the liquid may be passed, at the upper part, by latching the disc-like porous member 119 to the step 115.

In each pipette tip 110, the opening 118 on the tip of the narrow diameter tube 109 is occluded by the detachable cap 27. On the other hand, with regard to the attachment opening 104, there are three kinds of the pipette tips each having a support and a fluid enclosed therein 105, 121 and 123, including the case where the pipette tip each having a support and a fluid enclosed therein 105 and 123 are each attached to the nozzle via the connecting tube 29 or 53 as shown in FIGS. 4 (a) and (c), and the case where the pipette tip having a support and a fluid enclosed therein 121 is directly attached to the nozzle as shown in FIG. 4 (b). In the pipette tips each having a support and a fluid enclosed therein 105, 121 and 123, the cap 27 used for enclosing the fluid for sustainedly activating the support 32, the connecting tubes 29 and 53 to be provided to the attachment opening 104, and the seal 43 are similar to those provided to the pipette tips 20, 70 and 80 as explained in the first to third embodiments, and thus the explanation thereof is not repeated here.

Figure 5:
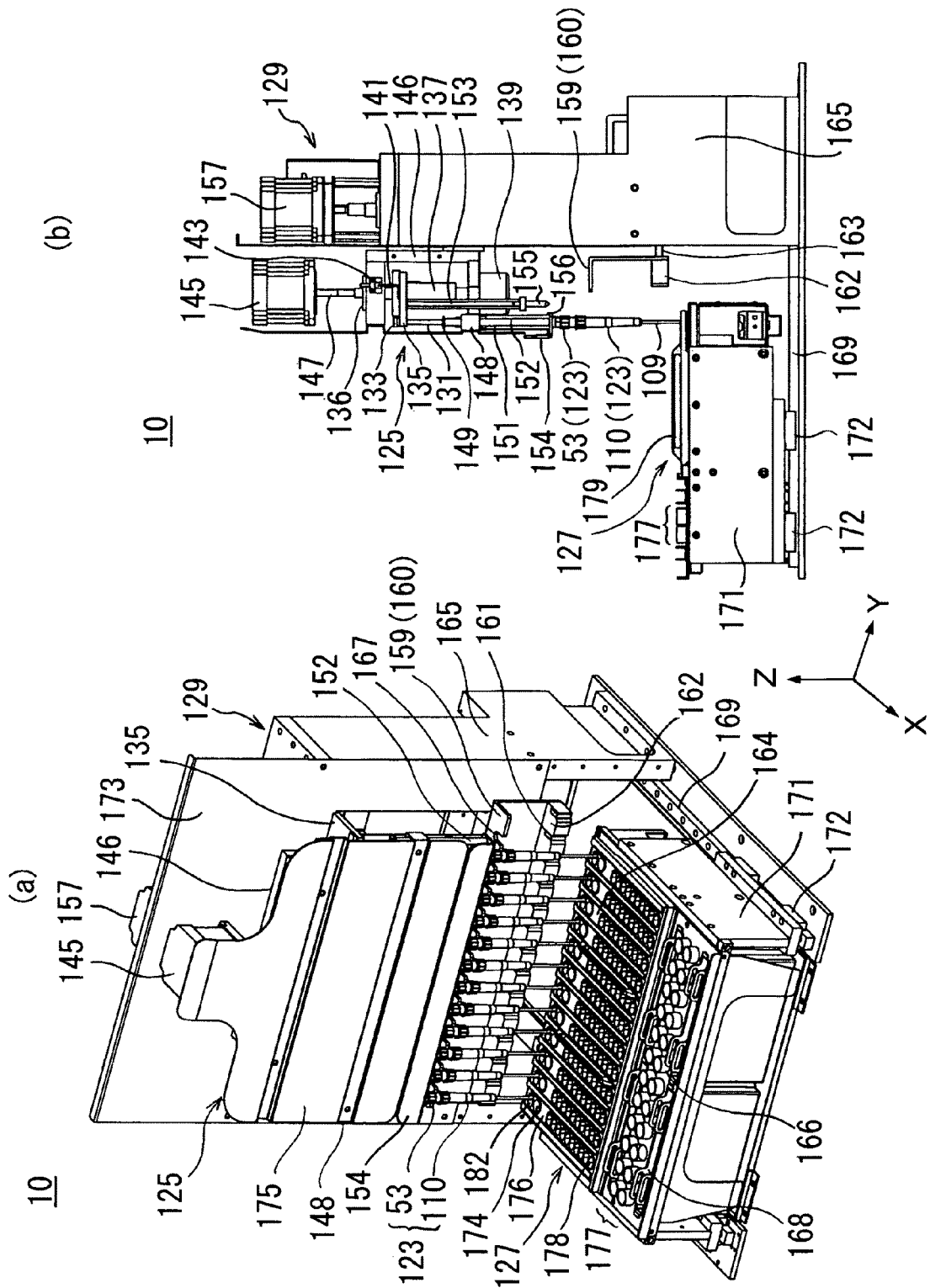
FIG. 5 is a drawing showing an apparatus for treating a pipette tip having a support and a fluid enclosed therein according to a fifth embodiment of the present invention.

Next, FIG. 5 shows a perspective view and a side view showing the apparatus for treating the pipette tips each having a support and a fluid enclosed therein 10 according to the fifth embodiment of the present invention.

The apparatus for treating the pipette tips each having a support and a fluid enclosed therein 10 has a mechanism for sucking and discharging a gas comprising, for example, the nozzle head 125 having a series of multiple nozzles (in this case, 12 nozzles) (corresponds to the symbol 199 in FIG. 8) to which the pipette tips each having a support and a fluid enclosed therein 123 are to be attached to perform sucking and discharging treatment with respect to the pipette tips each having a support and a fluid enclosed therein 123; accommodating part group 127 in which various liquid accommodating parts for accommodating the solution comprising various samples, reagents and the like to be sucked in the pipette tips each having a support and a fluid enclosed therein 123 or discharged from the pipette tips each having a support and a fluid enclosed therein 123, or the tip accommodating parts in which the pipette tips each having a support and a fluid enclosed therein are to be accommodated, are arrayed in a matrix; and the transfer mechanism 129 as a transfer means for relatively transferring between the nozzle head 125 and the accommodating part group 127 in the horizontal direction (in this case, X-axial direction) and the vertical direction (in this case, Z-axial direction).

To the nozzle head 125 are provided with a row of twelve nozzles arrayed in a line (along the Y axial direction) that are attached via their connecting tubes 53 with respect to the twelve pipette tips each having a support and a fluid enclosed therein 123. To the upper side of the nozzles are provided with the twelve cylinders 151 each communicates with each nozzle. In each of the twelve cylinders 151 is slidably provided with a plunger (not depicted), and the plungers are concurrently driven by the twelve rods 131 in the vertical direction.

The rod head parts 133 on the upper ends of the twelve rods 131 are fixed and supported on the driving plate 135 in the state that they pass through to the upper side of the driving plate 135. To the driving plate 135 are attached the twelve hexagonal column-like hexagonal supporting columns 153 so that the rods 131 are aligned in the Y axial direction at the same array interval as the rods 131 at the position apart from the rod array arrayed along the Y axial direction at a predetermined distance along the X axial direction, and are extended to the lower side. The perforation needles 155 for perforating the seals 57 of the pipette tips each having a support and a fluid enclosed therein 123 protrude downward from the lower ends of the hexagonal supporting columns 153.

The driving plate 135 is screwed in the ball screw 147 that is rotatably driven by the motor for sucking and discharging 145 provided to the Z axial transfer body 146 that is supported transferably in the Z axial direction by the fixed base part 165 of the apparatus for treating the pipette tips each having a support and a fluid enclosed therein 10, and fixed to the nut part 137 that moves vertically by rotation of the ball screw 147. The ball screw 147 is axle bore by the bearing 136 provided to the Z axial transfer body 146 and the ball screw bearing 139 provided to the lower side of the Z axial transfer body 146.

To the driving plate 135 is provided with the light shielding plate 141 that extends in the vertical direction. Where the driving plate 135 reaches the upper limit position of the rods 131, the light shielding plate 141 blocks the light from the light-emitting member provided to the base part 165 and prevents the light from reaching the light-receiving member.

To the lower side of each cylinder 151 is provided with the plate having L-shaped cross section 154 on which a pore (not depicted) is provided along the longitudinal direction of the horizontal plate 156; the pore has such a size that the nozzle may pass the pore but the connecting tube 53 or the pipette tip 110 of the pipette tip having a support and a fluid enclosed therein 123 may not pass. To the both ends of the horizontal plate 156 are each provided the tube-like supporting column 152 that supports the L-shaped plate 154 as a tip detaching part. The twelve cylinders 151 are fixed to the cylinder supporting member 148 at their upper ends and are supported so as to extend downward. The two supporting columns 152 penetrate the cylinder supporting member 148 and go through the upper side, and to each upper end is provided with the flange 149.

The driving plate 135 performs suction and discharging of the gas, or perforation of the seal 57 of the pipette tip having a support and a fluid enclosed therein 123 using the perforation needle 155, by reciprocating the rod 131 between the upper limit position and the flange 149, but the driving plate 135 may further be lowered to a level lower than the level of the flange 149 and reach the lower limit position. In such case, the driving plate 135 lowers together with the flange 149, whereby the supporting column 152 is pushed and the L-shaped plate 154 is descended, and the pipette tips each having a support and a fluid enclosed therein 123 are squeezed through the nozzle and drop off.

The case where the pipette tip having a support and a fluid enclosed therein 123 is attached to the nozzle is mentioned below. Here, the nozzle, the cylinder 151, the rod 131, the motor for sucking and discharging 145, the ball screw 147, the nut part 137 and the like correspond to the sucking and discharging mechanism.

To the base part 165 of the apparatus for treating the pipette tips each having a support and a fluid enclosed therein 10 are provided with the Z axial motor 157 as the transfer mechanism 129 for transferring the Z axial transfer body 146 of the nozzle head 125 in the vertical direction; twelve lines of the cartridge containers 176 provided with multiple (in this case, twelve) accommodating parts to which the narrow diameter tubes 109 of the pipette tips each having a support and a fluid enclosed therein 123 may be inserted, as the accommodating part group 127; the tip accommodating part 177 that may accommodate twenty-four pipette tips each having a support and a fluid enclosed therein 123; and the transfer mechanism (not depicted) that transfers the stage provided along the transfer trajectory of the twelve nozzles along the X axial direction, in the X axial direction.

Furthermore, the base part 165 has the reverse L-shaped drop-off preventing part 160 that is provided contactably and discontactably with respect to the twelve pipette tips each having a support and a fluid enclosed therein 123 attached to the nozzles in the X axial direction, and the magnetic part 162 provided to the lower side thereof; the actuator 163 that transfers the drop-off preventing part 160 and the magnetic part 162 in the X axial direction; and the motor (not depicted) for driving the actuator. In the magnetic part 162, the magnets 161 are embedded in the twelve grooves arrayed at the same array intervals as that of the pipette tips each having a support and a fluid enclosed therein 123 along the prismatic column-shaped member extending in the Y axial direction, and the direction from the magnets 161 that contact and discontact to the corresponding pipette tips each having a support and a fluid enclosed therein 123 is the X axial direction. The drop-off preventing part 160 has the horizontal engaging plate 159 that has the twelve approximately half circular notch parts 167 arrayed at the same positions and the same array intervals (distances between the centers) as the pipette tips each having a support and a fluid enclosed therein 123 along the Y axial direction. The diameter of the half circle is larger than that of the reservoir tube 107 of the wide diameter tube 106 of the pipette tip having a support and a fluid enclosed therein 123, but smaller than the diameter including the height of the protrusion 112.

The accommodating part group 127 has the box body 171, the four sliders 172 provided to both sides of the lower part of the box body 171 along the Y axial direction, and two guide rails 169 that engage with the sliders 172 to transferably guide the box body 171 along the X axial direction.

The box body 171 has the container rack 164 in which the liquid accommodating part 178 (for example, it has ten wells from well w1 to well w10) that accommodates a solution comprising various samples, reagents and the like to be sucked or discharged with respect to the pipette tip having a support and a fluid enclosed therein 123, the accommodating part 174 that enables temperature control, and the twelve cartridge-like containers 176 in which the accommodating part for measurement 182 that enables measurement are arrayed in a line, are arrayed along the Y axial direction at the same array intervals as the array intervals of the nozzles while conforming their longitudinal direction to the X axial direction; and the tip rack 166 in which two arrays of the twelve tip accommodating parts 177 that accommodate the pipette tips each having a support and a fluid enclosed therein 123 and the pipette tips 110 are arrayed at the same array intervals as the array interval along the Y axial direction. To the container rack 164 and the tip rack 166 is each provided with the handles 179 and 168 for gripping. Although it is not depicted, a light measuring apparatus for measuring the luminescence in the accommodating part for measurement or the tips is provided.

Figure 6:
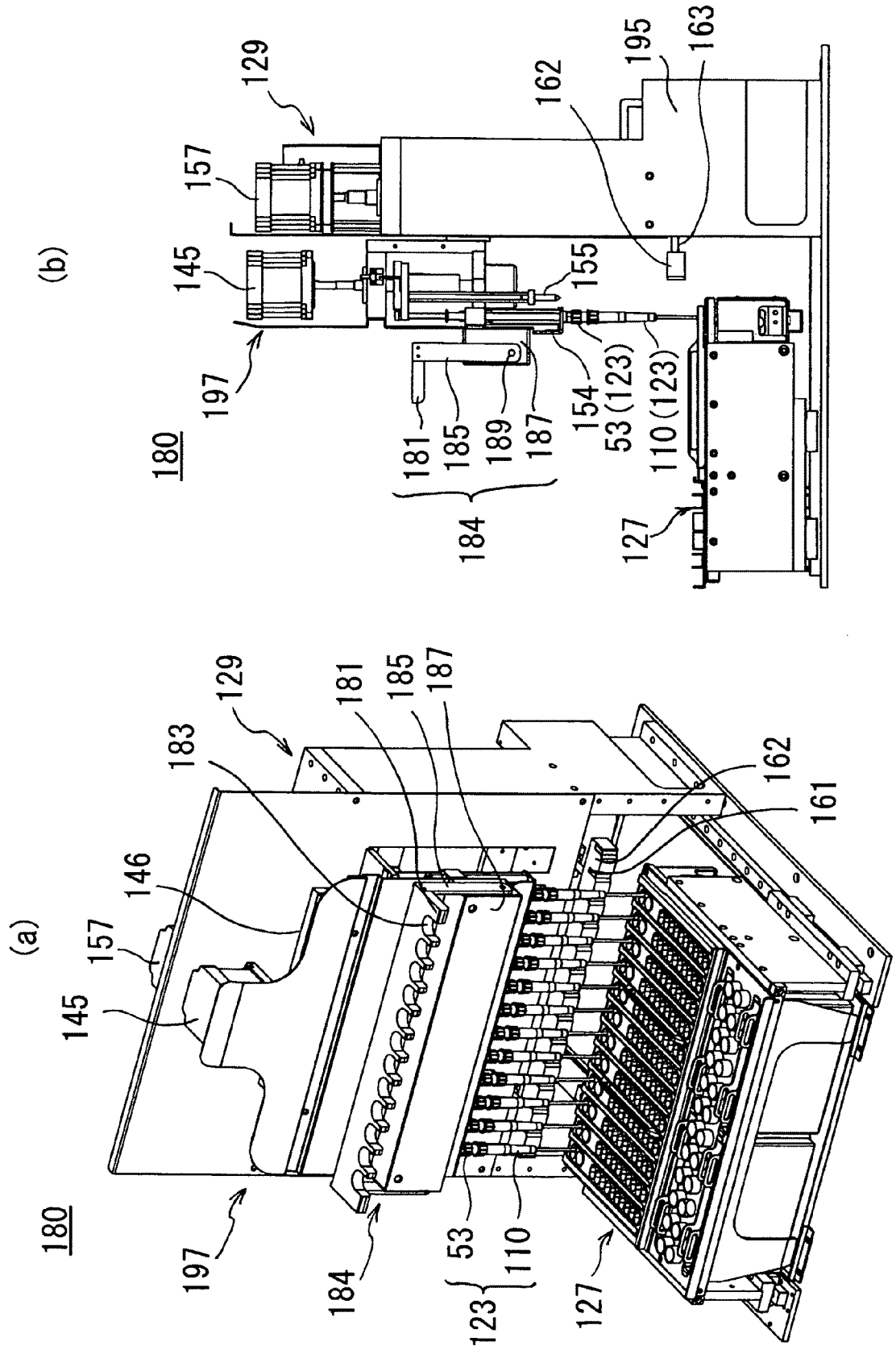
FIG. 6 is a drawing showing an apparatus for treating the pipette tip having a support and a fluid enclosed therein according to a sixth embodiment of the present invention.

Next, based on FIG. 6, the apparatus for treating a pipette tip having a support and a fluid enclosed therein 180 according to the sixth embodiment is explained. The same symbols or the same diagrammatic drawings as those in FIG. 5 represents the same symbols and diagrammatic drawings, and thus the explanation thereof is not repeated here.

The apparatus for treating a pipette tip having a support and a fluid enclosed therein 180 according to this embodiment has a mechanism for sucking and discharging a gas, comprising, for example, the nozzle head 197 having a series of multiple (in this case, twelve) nozzles (see FIG. 8, 199) to which the pipette tips each having a support and a fluid enclosed therein 123 are attached to perform sucking and discharging treatment with respect to pipette tips each having a support and a fluid enclosed therein 123; the accommodating part groups 127; and the transfer mechanism 129.

Unlike the nozzle head 125 mentioned above, the drop-off preventing part 184 is attached to the nozzle head 197 itself. The drop-off preventing part 184 has the rotary engaging plate 181 having the twelve approximately hemicircular notch parts 183 that are arrayed in the Y axial direction at the same array intervals as the pipette tips each having a support and a fluid enclosed therein 123 along the Y axial direction; the two arms 185, each of which is fixed at its one end on the both ends of the rotary engaging plate 181, are extending from the rotary engaging plate 181 to the orthogonal direction, and each of which has the rotation center 189 at the other end; and the motor accommodating part 187 in which a motor for rotating the arms 185 is accommodated.

On the other hand, the base part 195 of the apparatus for treating a pipette tip having a support and a fluid enclosed therein 180 is provided with the magnetic part 162 that is contactably and discontactably provided along the X axial direction with respect to each of the twelve pipette tips each having a support and a fluid enclosed therein 123 attached to the nozzles; the actuator 163 for transferring the magnetic part 162 along the X axial direction; and a motor (not depicted) for driving the actuator. In the magnetic part 162, the magnets 161 are embedded in the twelve grooves arrayed at the same intervals as that of the pipette tips each having a support and a fluid enclosed therein 123 along the prismatic column-shaped member as mentioned above, and the magnets 161 contact and discontact along the X axial direction with respect to the pipette tips each having a support and a fluid enclosed therein 123.

Figure 7:
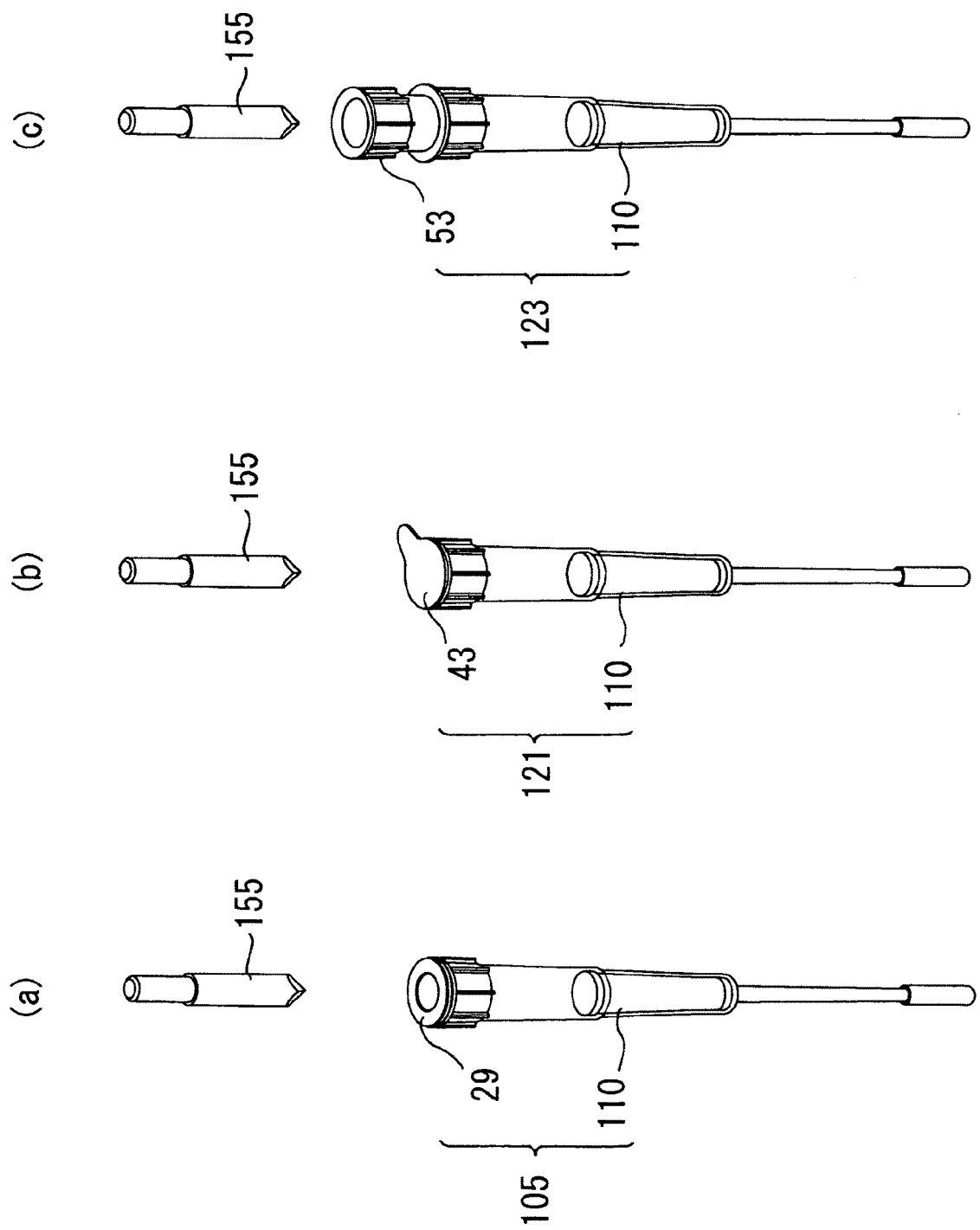
FIG. 7 is a drawing showing the perforation operation of the pipette tip having a support and a fluid enclosed therein in the apparatus for treating the pipette tip having a support and a fluid enclosed therein according to the fifth embodiment of the present invention.

FIG. 7 shows the relationship between the perforation needles 155 provided to the apparatuses for treating the pipette tips each having a support and a fluid enclosed therein 10 and 180 according to the fifth and sixth embodiments, and the pipette tips each having a support and a fluid enclosed therein 105, 121 and 123.

Figure 8:
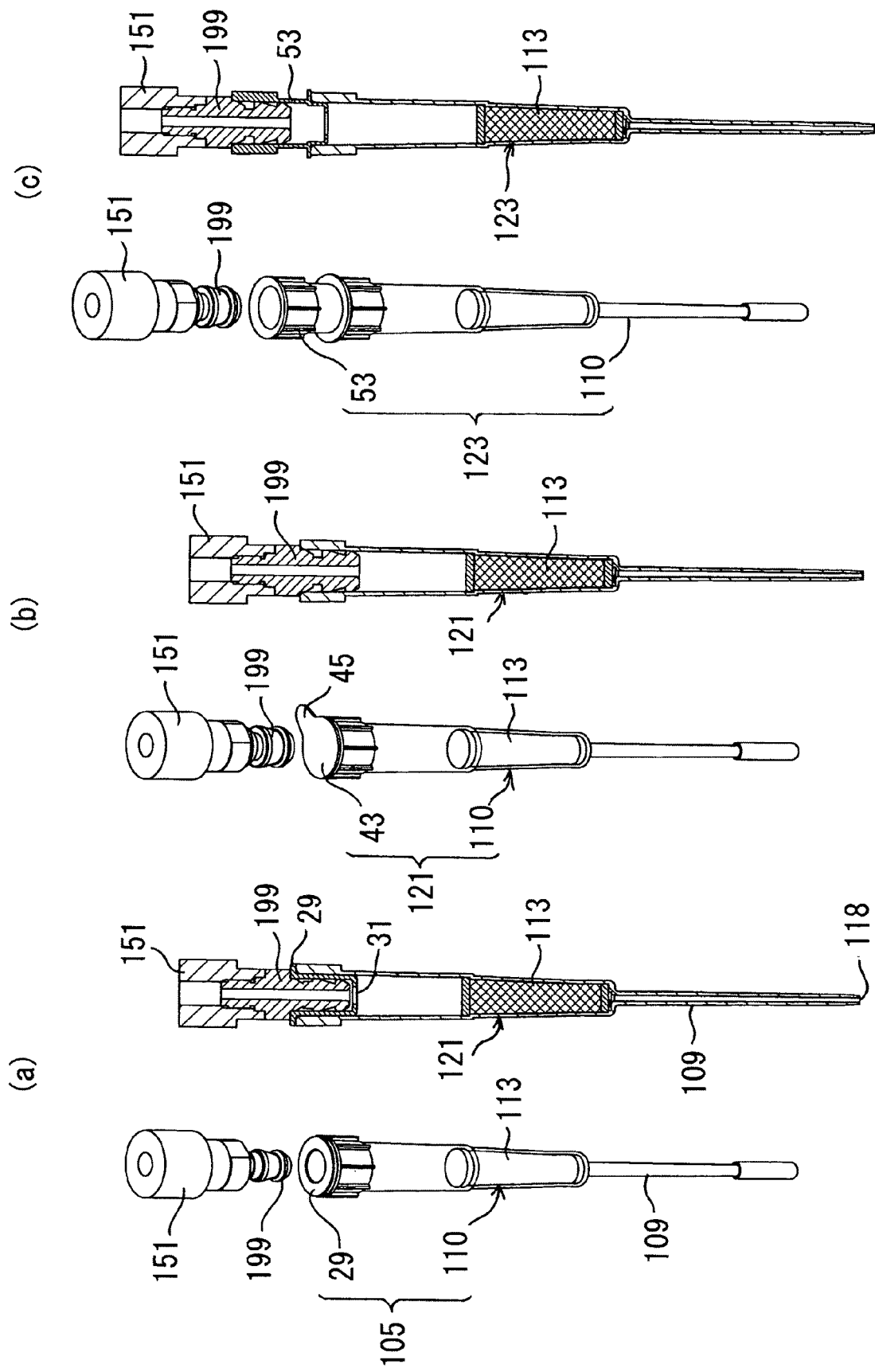
FIG. 8 is a drawing showing the attaching operation of the pipette tip having a support and a fluid enclosed therein in the apparatus for treating the pipette tip having a support and a fluid enclosed therein according to the fifth embodiment of the present invention.

FIG. 8 shows examples wherein the pipette tips each having a support and a fluid enclosed therein 105, 121 and 123 are attached to the nozzles 199 of the apparatuses for treating the pipette tips each having a support and a fluid enclosed therein 10 and 180 according to the fifth (or sixth) embodiment. In order to attach the pipette tips each having a support and a fluid enclosed therein 105, 121 and 123, any of the twelve pipette tips each having a support and a fluid enclosed therein 105, 121 or 123 (naturally, other pipette tips each having a support and a fluid enclosed therein 11, 41, 51, 61, 73, 75, 77, 101 or 103 may be used) are accommodated in advance in the twelve tip accommodating parts 177 arrayed in the tip rack 166 of the accommodating part group 127.

The box body 171 is transferred in the X axial direction so that the twelve pipette tips each having a support and a fluid enclosed therein 105 (121 or 123) are positioned below the twelve perforation needles 155 of the apparatus for treating the pipette tips each having a support and a fluid enclosed therein 10. The Z axial motor 157 provided to the base part 165 is then rotary driven to lower the Z axial transfer body 146, and is lowered to the height that may reach the seals 33 of the connecting tubes 29 provided to the upper ends of the pipette tips each having a support and a fluid enclosed therein 105 using the driving plate 135 of the perforation needles 155. The driving plate 135 is then lowered to concurrently perforate the twelve seals 33 provided to the twelve pipette tips each having a support and a fluid enclosed therein 105 by the twelve perforation needles 155.

The twelve pipette tips each having a support and a fluid enclosed therein 105 provided with the perforated seals 33, which are accommodated in the tip accommodating part 177, are then transferred to just below the nozzles 199 of the apparatus for treating the pipette tips each having a support and a fluid enclosed therein 10 using the transfer mechanism 129. The Z axial transfer body 146 is then inserted in the connecting tube 29 so as to be fit and attached by lowering the nozzles 199 by driving the Z axial motor 157.

Figure 9:
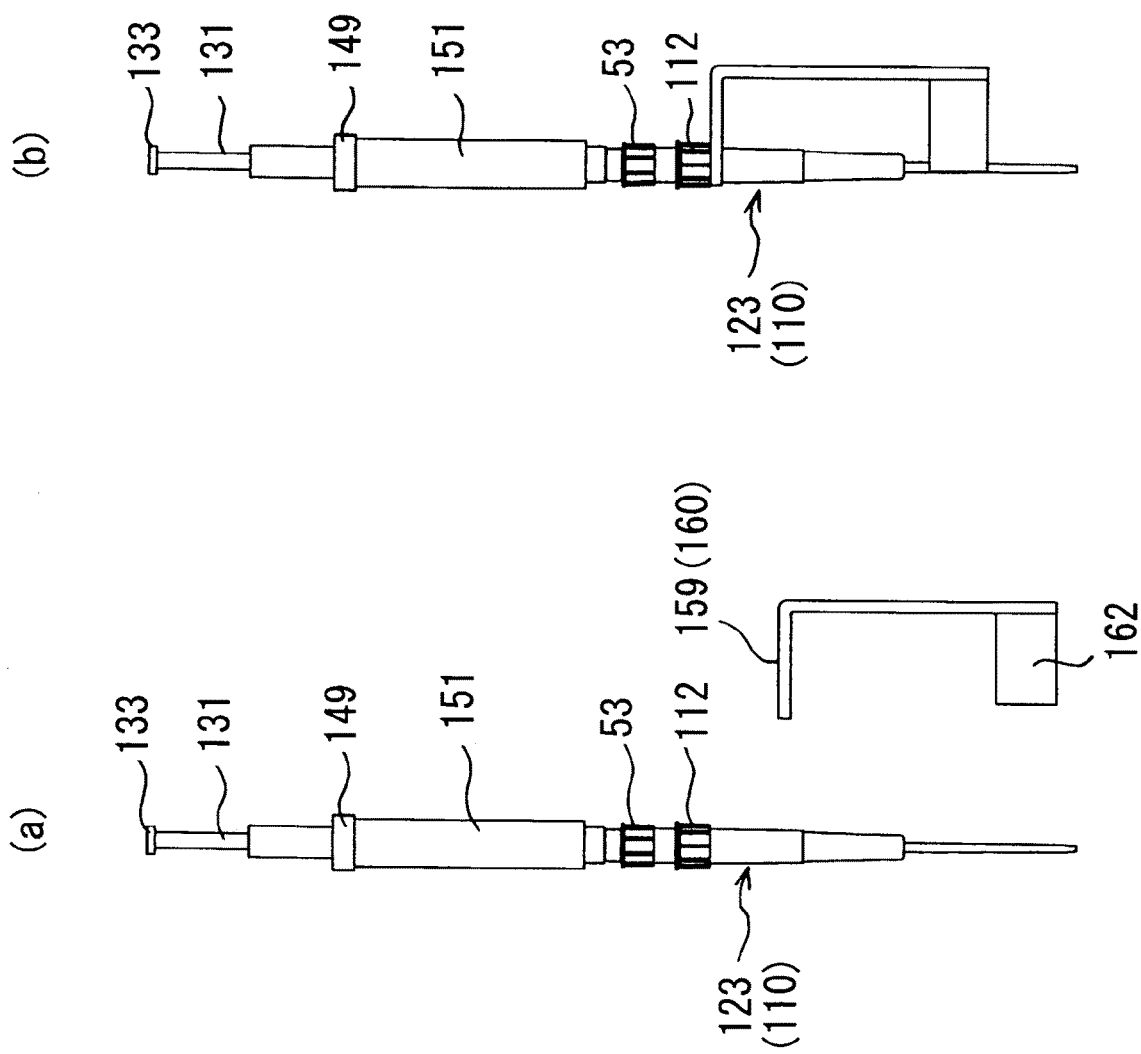
FIG. 9 is a drawing showing the drop-off preventing operation in the apparatus for treating the pipette tip having a support and a fluid enclosed therein according to the fifth embodiment of the present invention.

Next, based on FIG. 9, the case where the inside of the pipette tips each having a support and a fluid enclosed therein 123 attached to the nozzles is pressurized using the apparatus for treating the pipette tips each having a support and a fluid enclosed therein 10 is explained.

Where the inside of the pipette tips each having a support and a fluid enclosed therein 123 is pressurized, the driving plate 135 (see FIG. 5) in which the plunger accommodated in the cylinder 151 that communicates with the nozzle to which the pipette tip having a support and a fluid enclosed therein 123 is attached is connected to the rod 131 is moved downward by rotary driving the motor for sucking and discharging 145 (see FIG. 5). During this time, the drop-off preventing part 160 is approached by transferring it in the obliquely upward direction relative to the pipette tip having a support and a fluid enclosed therein 123; the hemicircular notch part 167 (see FIG. 5) of the horizontal engaging plate 159 engages with the reservoir tube 107 of the wide diameter tube 106 of the pipette tip having a support and a fluid enclosed therein 123; and the upper surface of the horizontal engaging plate 159 engages with the lower end of the protrusions 112 provided to the pipette tip having a support and a fluid enclosed therein 123, whereby the pipette tip having a support and a fluid enclosed therein 123 is supported.

Figure 10:
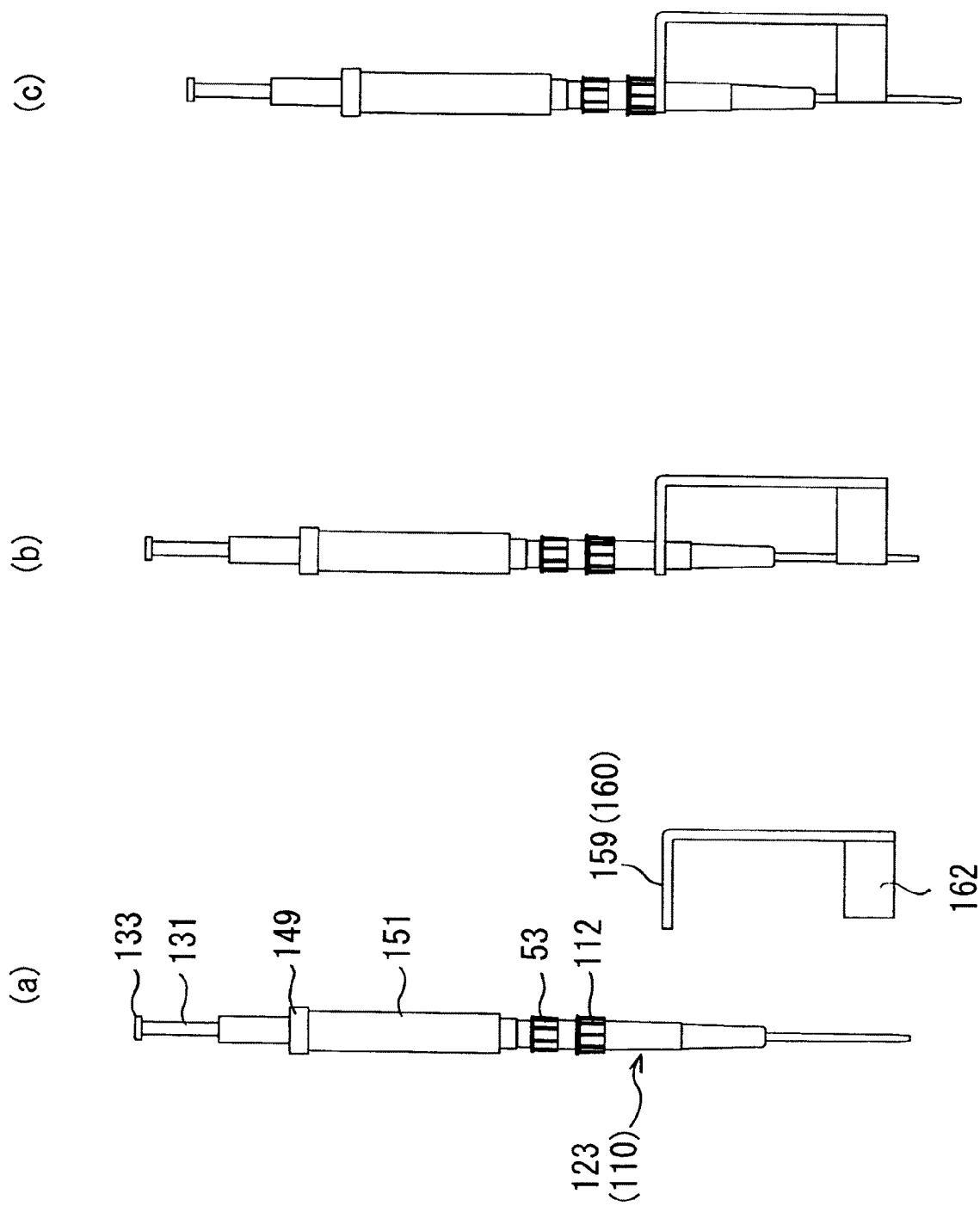
FIG. 10 is a drawing showing other drop-off preventing operation in the apparatus for treating the pipette tip having a support and a fluid enclosed therein according to the fifth embodiment of the present invention.

On the other hand, in the case as shown in FIG. 10, during the above-mentioned pressurization, the drop-off preventing part 160 is approached by transferring it in the horizontal direction relative to the pipette tip having a support and a fluid enclosed therein 123; the hemicircular notch part 167 of the horizontal engaging plate 159 engages with the reservoir tube 107 of the wide diameter tube 106 of the pipette tip having a support and a fluid enclosed therein 123; and the pipette tip having a support and a fluid enclosed therein 123 is lowered to be engaged with the lower end of the protrusions 112, whereby the pipette tip having a support and a fluid enclosed therein 123 is supported.

Figure 11:
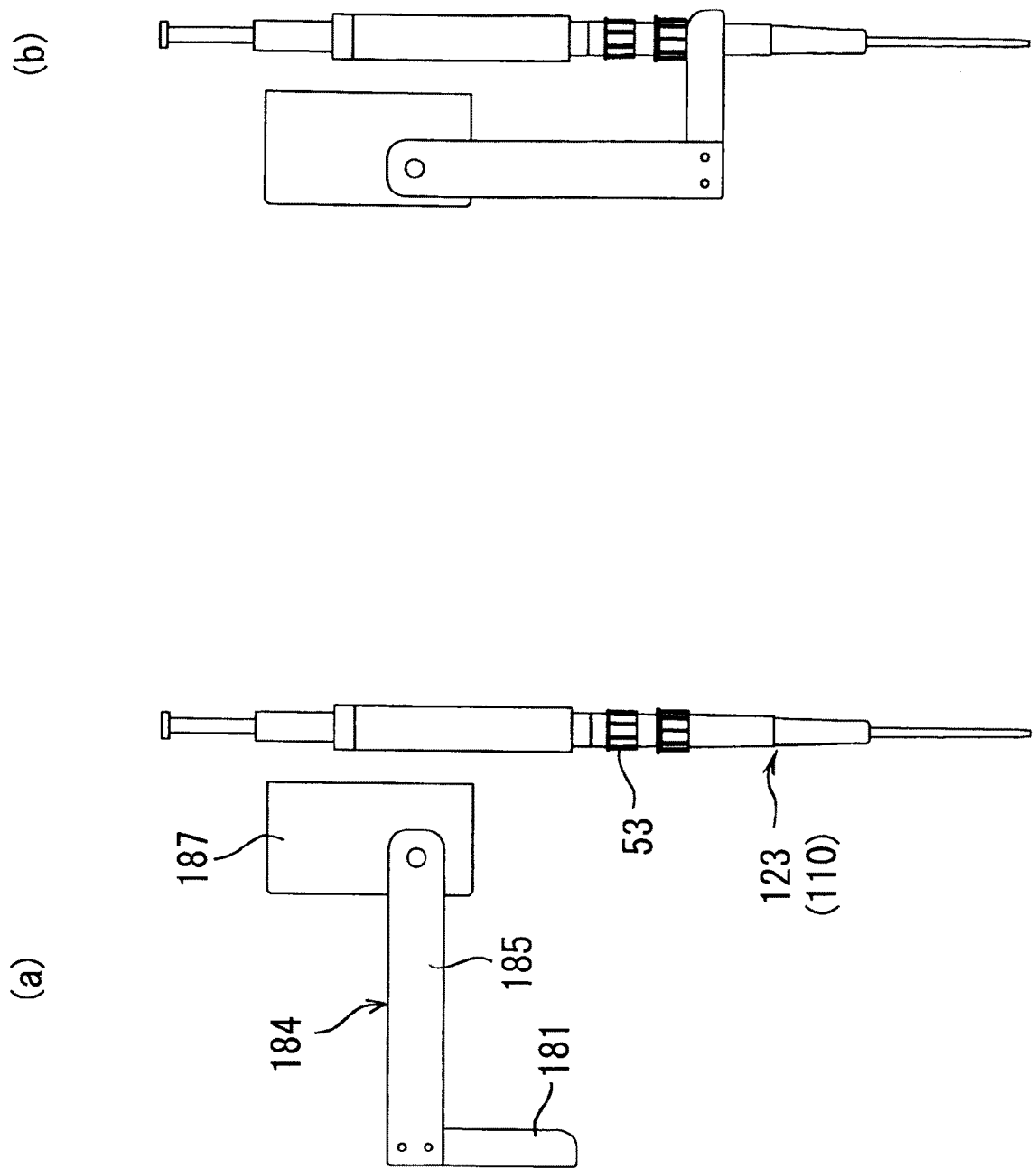
FIG. 11 is a drawing showing the drop-off preventing operation in the apparatus for treating the pipette tip having a support and a fluid enclosed therein according to the sixth embodiment of the present invention.

Next, based on FIG. 11, the case where the inside of the pipette tip having a support and a fluid enclosed therein 123 attached to the nozzle is pressurized using the apparatus for treating pipette tips each having a support and a fluid enclosed therein 180 is explained.

During pressurization, the rotary engaging plate 181 of the drop-off preventing part 184 is approached the pipette tip having a support and a fluid enclosed therein 123 by rotating the rotary engaging plate 181 by approximately 90° using a motor accommodated in the motor accommodating part 187; the hemicircular notch part 183 of the rotary engaging plate 181 engages with the reservoir tube 107 of the wide diameter tube 106 of the pipette tip having a support and a fluid enclosed therein 123, and engages with the surface on the side of the rotation center of the rotary engaging plate 181 and the lower end of the protrusions 112 of the pipette tip having a support and a fluid enclosed therein 123, whereby the pipette tip having a support and a fluid enclosed therein 123 is supported.

Figure 12:
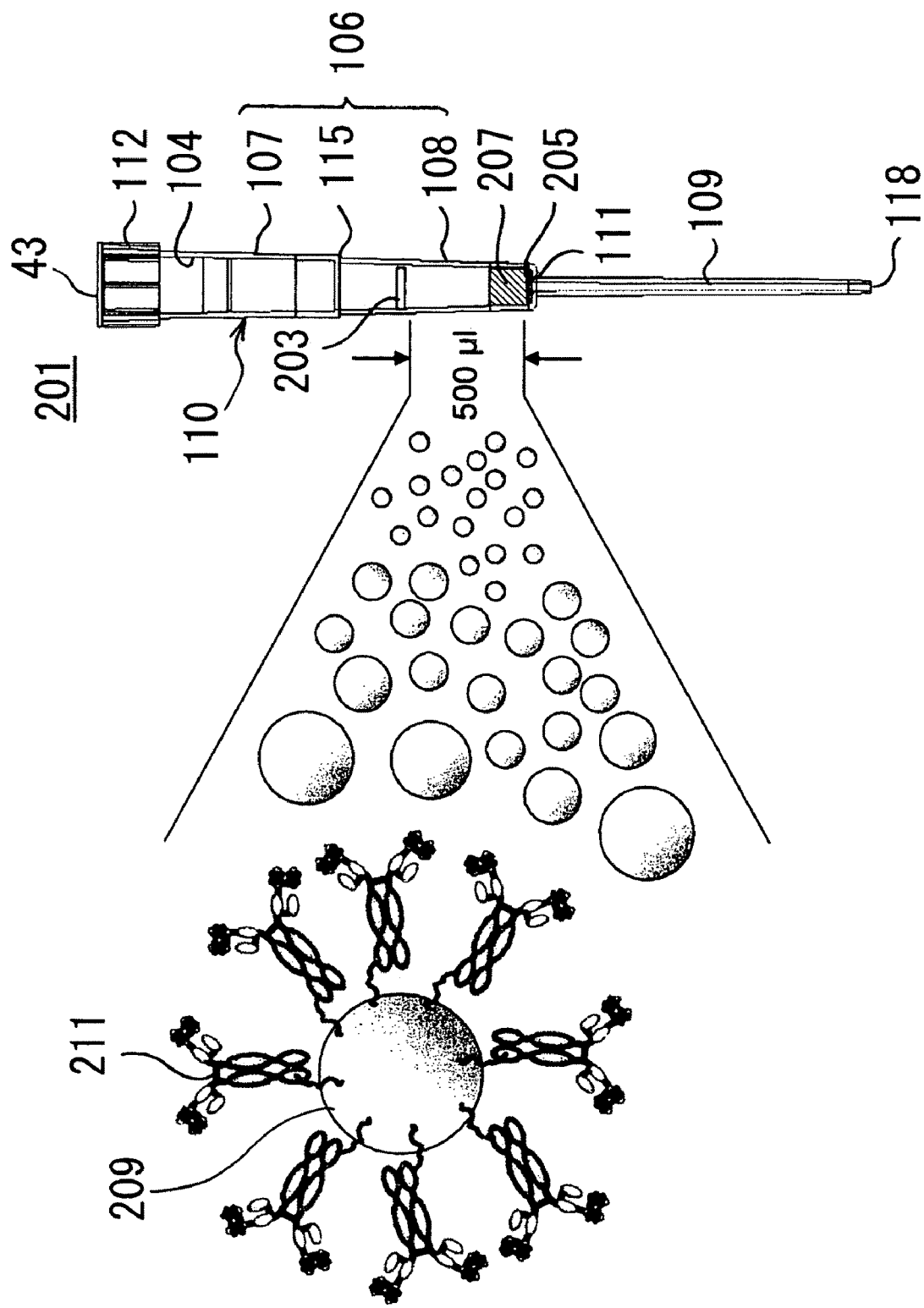
FIG. 12 is a drawing showing a pipette tip having a support and a fluid enclosed therein according to a seventh embodiment of the present invention.
Figure 13:
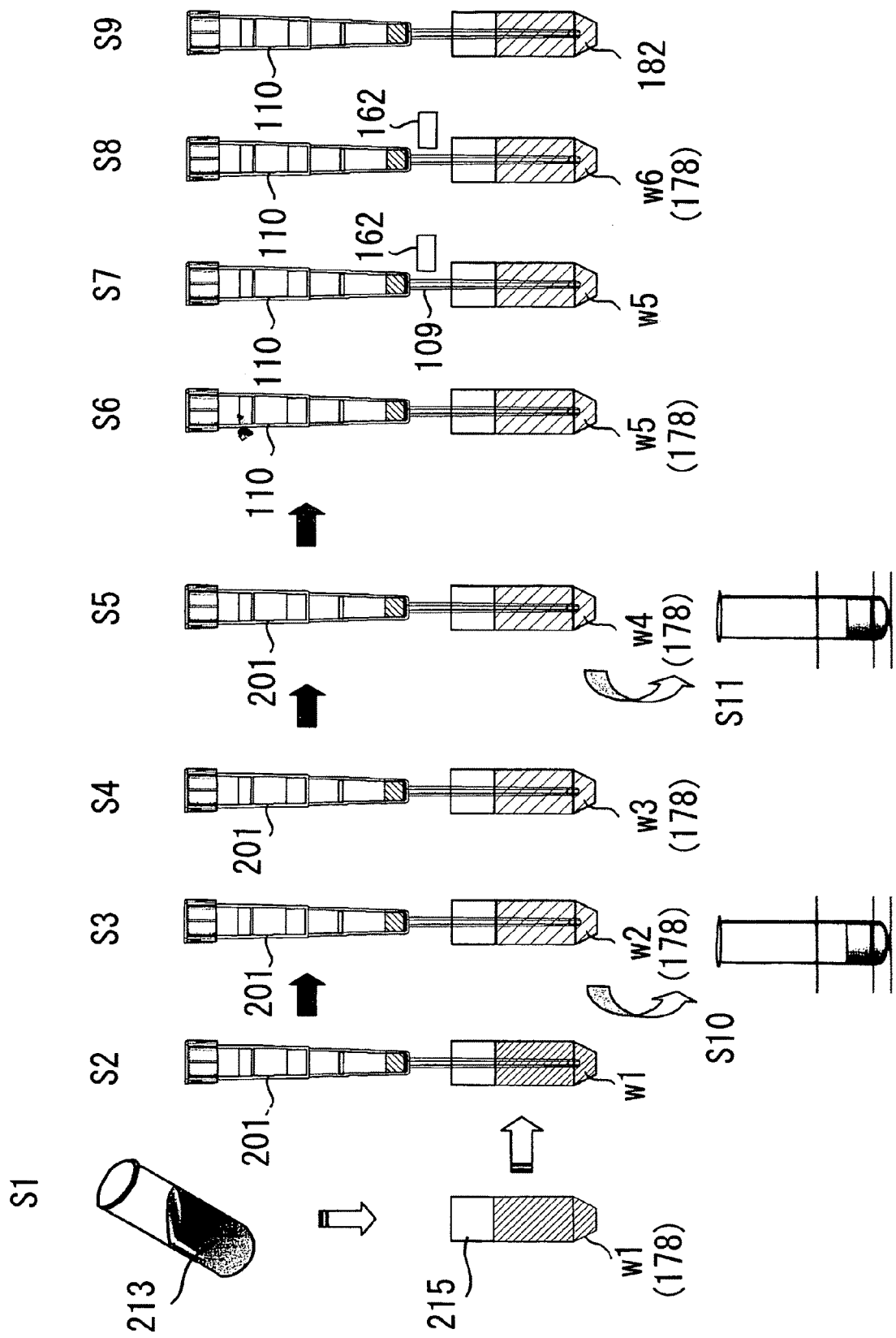
FIG. 13 is a treatment flow diagram according to an eighth embodiment of the present invention.

Next, using FIGS. 12 and 13, the treatment for separation of proteins using the pipette tip having a support and a fluid enclosed therein 201 for separating useful proteins by specifically separating, removing or the like of major proteins such as albumin and immunoglobulin from whole blood is explained. Human plasma proteome has been considered to be important as a studying method for finding clinical markers (for example, cancer-related antibodies and the like) that are useful for the diagnosis of diseases and management of therapies. Plasma is an important diagnosis sample, and clinical markers are explored as the targets of human clinical proteome analysis. Plasma encompasses various "plasma proteins", and the concentration thereof are widely distributed according to the kinds of plasma proteins. Serum albumin is included by the largest amount in blood and is included by 30 to 50 mg per 1 milliliter of blood. Furthermore, blood also includes various different immunoglobulins (IgM, IgG, IgA, IgE and IgD). Where a trace amount of the proteins in plasma is analyzed, proteins included by a large amount such as albumin prevents the detection and quantification of the trace proteins. Therefore, where an analysis is performed, it is necessary to remove these major proteins by a certain method.

Here, the pipette tip having a support and a fluid enclosed therein 201 encloses particulate supports in which IgY (an antibody of Chiken-IgY avian) is bonded on the surfaces of many microparticles 209 instead of cylindrical block-like support 113 as mentioned above in the support accommodate tube 108 in the wide diameter tube 106 of the above-mentioned pipette tip 110. As the microparticles 209, those having a diameter of about several hundred micrometers are adopted. The step of the transition part 111 at the lower side of the above-mentioned wide diameter tube 106 is latched the porous member 205 made of polyethylene having a diameter of 5 mm and a pore diameter of 80 to 100 μm of the disk-like pore that allows passage of the liquid but does not allow passage of the above-mentioned microparticles 209, and hold by pressing from above using the stainless stopper 207. Furthermore, the porous member 203 made of polyethylene having a pore diameter of 80 to 100 μm and a diameter of 7 mm having a disk-like shape through which the liquid may be passed but the microparticles 209 may not be passed is hold by latching on the upper side of the wide diameter tube 106, utilizing the tapered slope of the wide diameter tube 106. Many microparticles 209 on which IgY has been bonded are enclosed between the porous members 203 and 205. Furthermore, the attachment opening 104 is occluded by covering with the seal 43. The opening 118 at the tip is occluded by a cap, and a predetermined buffer solution as the fluid for sustainedly activating the support is enclosed between them. The microparticles 209 are suspended in the buffer solution existing between the porous members 203 and 205 and are considered to have a volume of about 500 microliters as a whole.

Based on FIG. 13, the treatment for separation of above-mentioned proteins using the apparatus for treatment of the pipette tips each having a support and a fluid enclosed therein 10 in which the pipette tips each having a support and a fluid enclosed therein 201 are attached to the nozzles is explained.

In Step S1, whole blood is collected from twelve subjects, and 20 μl of which is sucked in advance by attaching the pipette tips to the nozzles of the apparatus for treatment of the pipette tips each having a support and a fluid enclosed therein, or by using other pipetting apparatus, and dispensed into the twelve wells w1 aligned along the Y axial direction of the liquid accommodating part 178 in the accommodating part group 127 of the apparatus for treatment of the pipette tips each having a support and a fluid enclosed therein 10. A saline treated with a buffer for dilution such as Tris buffer (TBS, pH 7.4) is then dispensed to the wells w1 so as to dilute the whole blood to 500 μl as a whole.

In step S2, the box body 171 of the accommodating part group 127 is transferred to the X axial direction with respect to the nozzle head 125 so that the perforation needles 155 are positioned above the twelve pipette tip accommodating parts 177 in which the twelve pipette tips each having a support and a fluid enclosed therein 201 are accommodated. The Z axial motor 157 provided to the base part 165 is then rotary driven to lower the Z axial transfer body 146, and is lowered to the height that may reach the seals 43 provided to the upper ends of the pipette tips each having a support and a fluid enclosed therein 201 using the driving plate 135 of the perforation needles 155. The driving plate 135 is then lowered to lower the twelve perforation needle 155 to pass and concurrently perforate the twelve seals 43 provided to the twelve pipette tips each having a support and a fluid enclosed therein 201.

The tip accommodating part 177 accommodating the twelve pipette tips each having a support and a fluid enclosed therein 201 having the perforated seals 43 are then transferred to just below the nozzles 199 of the apparatus for treating the pipette tips each having a support and a fluid enclosed therein 10 using the transfer mechanism 129. The nozzles 199 are concurrently inserted to the attachment openings 104 by the Z axial transfer body 146 by lowering the nozzles 199 by driving the Z axial motor 157, whereby the twelve pipette tips each having a support and a fluid enclosed therein 201 are concurrently attached to the twelve nozzles 199.

The cap 201 is then removed from the lower end of each pipette tip having a support and a fluid enclosed therein 201 by manually pulling it downward. At this time, the horizontal engaging plate 159 of the drop-off preventing part 160 is approached and engaged with the pipette tip having a support and a fluid enclosed therein 201 so as to support the pipette tip having a support and a fluid enclosed therein 201 at the lower side of the protrusions 112 to prevent dropping off from the nozzle 199. Furthermore, the pressure of the inside of the pipette tip having a support and a fluid enclosed therein 201 is maintained at negative pressure so that squirt of the fluid for sustainedly activating the support in the inner part is prevented.

Suction and discharging are repeated for 15 minutes by separating the horizontal engaging plate 159 of the drop-off preventing part 160 from the pipette tip having a support and a fluid enclosed therein 201; transferring the box body 171 to position the accommodating part for measurement 182 just below the attached pipette tip having a support and a fluid enclosed therein 201; lowering the Z axial transfer body 146 to insert the narrow diameter tube 109 of the pipette tip having a support and a fluid enclosed therein 201 into the accommodating part for measurement 182; and vertically moving the driving plate 135. In so doing, the horizontal engaging plate 159 of the drop-off preventing part 160 approaches and engages with the pipette tip having a support and a fluid enclosed therein 201, whereby the pipette tip having a support and a fluid enclosed therein 201 is supported. This allows binding of major proteins such as the above-mentioned albumin and immunoglobulin in blood to be removed to IgY on the surface of the microparticles 209 in the pipette tip having a support and a fluid enclosed therein 201 to remove the proteins from blood.

In Step S3, the pipette tips each having a support and a fluid enclosed therein 201 are pulled off from the accommodating part for measurement 182 by transferring them upward, and the box body 171 is transferred in the X axial direction and positioned just above the twelve wells w2 arrayed along the Y axial direction in the liquid accommodating part 178. A buffer for neutralization, 0.1 M Tris-HCl (pH 8.0) is accommodated as a washing fluid in the wells w2, and washing is performed by repeating suction and discharging eight times. In Step S10, a part is dispensed to other container so as to show the progression. Similarly, in Step S4, a buffer for neutralization, 0.1 M Tris-HCl (pH 8.0) is accommodated as a washing fluid in each well w3, and suction and discharging are each repeated by eight times. In this manner, the materials bonded to the microparticles 209 other than albumin are removed by washing.

In Step S5, the narrow diameter tube 109 is inserted to each well w4 while relatively transferring the pipette tip having a support and a fluid enclosed therein 201 to just above each well w4. Each well w4 accommodates a buffer liquid for dissociation, for example, 0.1M Glycine-HCl (pH 2.5), and suction and discharging are repeated eight times.

In this manner, the targets for removal such as albumin bonded to the microparticles 209 are dissociated from the microparticles 209 to the liquid. The solution containing the dissociated albumin and the like is transferred to other container in Step S11.

In Step S6, the pipette tips each having a support and a fluid enclosed therein 201 are relatively transferred to the first line of the tip accommodating part 177; the series of the twelve pipette tips each having a support and a fluid enclosed therein 201 are lowered by lowering the driving plate 135 of the L-shaped plate 154 as the tip detaching part from the nozzles 199 to concurrently detach the tips at the first line of the tip accommodating part 177; the series of the twelve nozzles 199 are relatively transferred to the second line of the tip accommodating part 177 in which the twelve pipette tips 110 are accommodated; and the nozzles 199 are pushed into and attached to the attachment openings by lowering the Z axial transfer body 146 using the Z axial motor 157. Using the pipette tip 110, the residual liquid in the well w1 is sucked and discharged by transferring it to the well w5. Furthermore, the material for predetermined bond, for example, the suspension liquid comprising many magnetic particles to which an antigen or antibody or the like has been fixed is mixed by transferring and discharging the liquid from a predetermined container to the well w4.

In Step S7, the target proteins, for example, cancer-related antibodies and the like in the liquid in which albumin and the like have been removed by the magnetic particles are further captured by the magnetic particles by repeating suction and discharging in the wells w5. During the step, an antigen or an antibody labeled with a luminescence material such as a fluorescent material or a chemical luminescence material, which is capable of bonding to the cancer-related antibody and the like, is suspended at the same time so as to react with or bond to the target protein. The magnetic parts 162 are concurrently approached the narrow diameter tubes 109 of the pipette tips 110 to apply a magnetic field so that the inner wall of the narrow tube adsorbs and separates the magnetic particles. In Step S8, the pipette tips 110 in which the magnetic particles are adsorbed on the inner wall are transferred to just above the wells w6 in which a buffer for neutralization, 0.1 M Tris-HCl (pH 8.0) is accommodated, while the magnetic field is applied, the twelve narrow diameter tubes 109 are concurrently inserted to the twelve wells w5, and suction and discharging are each repeated by ten times each, whereby the misplaced materials in the pipette tips 110 are removed.

In Step S9, the pipette tips 110 in which the magnetic particles are adsorbed by approaching the magnetic part 162 to apply a magnetic field, are transferred to the accommodating part for measurement 182 in which a predetermined luminescence liquid (substrate liquid in the case of chemical luminescence, or various liquids suitable for measurement in the case of fluorescent material) is accommodated and a light from outside is blocked, or the chemical luminescence and the like in the accommodating part for measurement 182 is measured in the state in which the magnetic particles are re-suspended, whereby capturing of the cancer-related antibody and the like may be confirmed.

The above-mentioned respective embodiments are specifically described for better understanding of the present invention, and not to be considered as limiting other embodiments. Therefore, modifications may be made without departing from the gist of the present invention. For example, in the above embodiments, only the case of proteins was mainly described, however DNA substances, RNA, sugar chains, or the like may also be used. Moreover, as to the particulate support, only the case of a spherical particulate support was described, however the present invention is not limited to this case, and the shape may be column-shape or rectangular-shape. Furthermore, the present invention may be applied to supports of indeterminate form. Moreover, the numerical values, the number of times, the shape, the number, the volume, and the like are also not limited to these cases.

The above respective components, pipette tip having a support and a fluid enclosed therein, support, pipette tip, enclosing part, nozzle, and other devices, may be optionally combined with appropriate modification.

The above-mentioned reagents and substances are merely exemplary, and other reagents and substances may be used. Moreover, the support capturing DNA or the like may be taken out from the narrow tube, and may be used as the object of preservation or other treatments. Furthermore, cases where the projections, the slopes, and the steps are provided in 1, 2, or 3 points in the pipette tip, are described, however the present invention is not limited to these cases and they may be provided in 4 points or more.

INDUSTRIAL APPLICABILITY

The present invention relates to a pipette tip having a support and a fluid enclosed therein, an apparatus for treating the pipette tip having a support and a fluid enclosed therein, and a method of treating the pipette tip having a support and a fluid enclosed therein. The present invention relates to various fields which require handling of biopolymer or biological low molecular materials such as genes, immune systems, amino acids, proteins, and sugars, for example, industrial fields, agricultural fields such as food, agricultural production, and fishery processing, pharmaceutical fields, medical fields such as sanitation, health, immunization, diseases, and genetics, scientific fields such as chemistry or biology, and the like. The present invention is an effective method particularly for continuously performing a series of treatments using a large number of reagents and substances in a predetermined order.

BRIEF DESCRIPTION OF THE REFERENCE SYMBOLS

Apparatuses for treating pipette tips each having a support and a fluid enclosed therein 10 and 180
Pipette tips each having a support and a fluid enclosed therein 11, 41, 51, 61, 73, 75, 77, 101, 103, 105, 121, 123 and 201
(Particles) 19, (wound bodies) 69 and 85, (microparticles) supports 113 and 209
Pipette tips 20, 70, 80 and 110
Connecting tubes 29 and 53
Fluid for sustainedly activating the support 32
Seals 33, 43 and 57

The invention claimed is:

1. A pipette tip having a support and a fluid enclosed therein having a function for sustainedly activating the support, comprising:
a pipette tip comprising an attachment opening that is to be attached to a nozzle for sucking and discharging a gas and capable of moving relative to an accommodating part group having a liquid accommodating part that accommodates or being capable of accommodating various liquids, or to a connecting tube that is attachable to the nozzle and communicated with the nozzle, and an opening that allows flow-in and flow-out of a liquid in response to the suction and discharging of the gas;
a support enclosed in the pipette tip, which adsorbs or captures a biological material in the liquid or reacts with or bonds to the biological material; and
a fluid for sustainedly activating the support, which comprises a predetermined liquid or a predetermined gas that is enclosed in the pipette tip in a breakable state and comes into contact with the support,
wherein the fluid for sustainedly activating the support is enclosed in a breakable state in the pipette tip by occluding the attachment opening by a perforable member or a detachable lid member or by attaching the attachment opening to the connecting tube in which a perforable member is provided so as to intersect the axial direction of the attachment tube, and by occluding the opening by a detachable cap;
wherein the pipette tip is provided with an enclosing part for enclosing the support in the pipette tip, and the enclosing part is provided to an area interposed between the perforable member provided to the attachment opening or the perforable member provided to the lid member or the attached connecting tube and the cap provided to the opening, and the liquid flown in the pipette tip and the enclosed fluid for sustainedly activating the support may pass the enclosing part; and
wherein the pipette tip has one or more of support passage preventing members that are provided separately from the pipette tip to partition between the opening and the attachment opening of the pipette tip so that the enclosing part becomes capable of contacting with the flow-in liquid or the enclosed fluid for sustainedly activating the support.

2. The pipette tip having a support and a fluid enclosed therein according to claim 1, wherein the pipette tip comprises a wide tube, a narrow tube that communicates with the wide tube, is provided to the lower side of the wide tube and is formed narrower than the wide tube, and a transition part between the wide tube and narrow tube; the attachment opening is provided to the upper side of the wide tube; and the opening is formed on the tip of the narrow tube.

3. The pipette tip having a support and a fluid enclosed therein according to claim 1, wherein the enclosing part has protruding parts projecting in the direction toward the inside, slopes tapered toward the opening, or steps projecting in the direction toward the inside toward the opening so that the inner wall surface of the pipette tip is partitioned between the attachment opening and the opening.

4. An apparatus for treating a pipette tip having a support and a fluid enclosed therein, comprising:
a nozzle head having one or multiple nozzles for sucking and discharging a gas;
a sucking and discharging mechanism by which the gas is sucked or discharged via the nozzles;
one or more pipette tips each having a support and a fluid enclosed therein and each having a function for sustainedly activating a support, which are to be attached to the nozzles or connecting tubes attachable to the nozzles to communicate or to be capable of communicating with the nozzles, each of which encloses a support that adsorbs or captures a biological material in the liquid or reacts with or bonds to the biological material and encloses a fluid for sustainedly activating the support that comprises a predetermined liquid or a predetermined gas in a breakable state and comes into contact with the support;
an accommodating part group provided with a tip accommodating part that accommodates or being capable of accommodating the pipette tips each having a support and a fluid enclosed therein, and a liquid accommodating part that accommodates or being capable of accommodating various liquids, and
a transfer means for transferring the nozzle head relative to the accommodating part group,
wherein the pipette tip having a support and a fluid enclosed therein comprises a pipette tip comprising an attachment opening that is to be attached to the nozzle or to the connecting tube and may be communicated with the nozzle, and an opening that allows flow-in and flow-out of a liquid in response to the suction and discharging of the gas; the support enclosed in the pipette tip; and a fluid for sustainedly activating the support that comprises a predetermined liquid or a predetermined gas that is enclosed in the pipette tip in a breakable state and comes into contact with the support, and the fluid for sustainedly activating the support is enclosed in a breakable state in the pipette tip by occluding the attachment opening of the pipette tip having a support and a fluid enclosed therein by a perforable member or a detachable lid member or by attaching the attachment opening to the connecting tube in which a perforable member is provided so as to intersect the axial direction of the attachment tube, and by occluding, the opening by a detachable cap; and
wherein the nozzle head is provided with a tip drop off-preventing part that engages with the pipette tip having a support and a fluid enclosed therein to support the pipette tip having a support and a fluid enclosed therein and prevents the pipette tip having a support and a fluid enclosed therein from dropping off from the nozzle when the pipette tip having a support and a fluid enclosed therein provided to the nozzle head is pressurized at a predetermined pressure through the nozzle.

5. The apparatus for treating the pipette tip having a support and a fluid enclosed therein according to claim 4, wherein the nozzle head has one or multiple perforation needles for perforating the perforable member and the perforation needles are provided so as to have a number identical to the number of the one or a series of multiple nozzles provided to the nozzle head, and mutual array intervals identical to the mutual array intervals between the nozzles.

6. The apparatus for treating the pipette tip having a support and a fluid enclosed therein according to claim 4, wherein the nozzle head is provided with a tip detaching part for detaching the pipette tip having a support and a fluid enclosed therein provided to the nozzle head from the nozzle.

7. The apparatus for treating the pipette tip having a support and a fluid enclosed therein according to claim 6, wherein the sucking and discharging mechanism, and one or both of the tip detaching part and a perforation needle driving part, are driven by shared use of an identical motor.

8. The apparatus for treating the pipette tip having a support and a fluid enclosed therein according to claim 4, wherein the apparatus for treating a pipette tip having a support and a fluid enclosed therein comprises at least one of a perforation needle and a tip detaching part, and a perforation operation of the perforation needle and the driving time or the driving position of the tip detaching part or the tip drop-off preventing part are controlled based on the substance condition and the treatment content.

9. The apparatus for treating the pipette tip having a support and a fluid enclosed therein according to claim 4, wherein the apparatus for treating a pipette tip having a support and a fluid enclosed therein is provided with a magnetic part capable of applying and removing a magnetic field in the axial direction of the nozzle along the vertical direction, on the lower side of the nozzle.

10. A method of treating a pipette tip having a support and a fluid enclosed therein for one or more pipette tips having a function for sustainedly activating the support each having a support and a fluid enclosed therein comprising a pipette tip comprising an attachment opening, which are to be attached to one or more nozzles for sucking and discharging a gas and capable of moving relative to an accommodating part group having a liquid accommodating part that accommodates or being capable of accommodating various liquids or to connecting tubes attachable to the nozzles and communicated with or may be communicated with the nozzles, and an opening that allows flow-in and flow-out of a liquid in response to the suction and discharging of the gas; a support enclosed in the pipette tip, which may adsorb or capture a biological material in the liquid or react with or bond to the biological material; and a fluid for sustainedly activating the support that comprises a predetermined liquid or a predetermined gas that is enclosed in the pipette tip in a breakable state and comes into contact with the support, wherein the method comprises a step of attaching the attachment opening or the connecting tube attached to the attachment opening to the nozzle, and a step of contacting, in which the attached pipette tip having a support and a fluid enclosed therein is transferred to a predetermined liquid accommodating part and the liquid accommodated in the liquid accommodating part is contacted with the support by sucking or discharging the liquid so that the support adsorbs or captures the biological material in the liquid or reacts with or bonds to the biological material, wherein the fluid for sustainedly activating the support is enclosed in a breakable state in the pipette tip by occluding the attachment opening by a perforable member or a detachable lid member or by attaching the attachment opening to the connecting tube in which a perforable member is provided so as to intersect the axial direction of the attachment tube, and by occluding the opening by a detachable cap;

wherein the pipette tip is provided with an enclosing part for enclosing the support in the pipette tip, and the enclosing part is provided to an area interposed between the perforable member provided to the attachment opening or the perforable member provided to the lid member or the attached connecting tube and the cap provided to the opening, and the liquid flown in the pipette tip and the enclosed fluid for sustainedly activating the support passes the enclosing part;

wherein the pipette tip has one or more of support passage preventing members that are provided separately from the pipette tip to partition between the opening and the attachment opening of the pipette tip so that the enclosing part becomes capable of contacting with the flow-in liquid or the enclosed fluid for sustainedly activating the support; and wherein the step of attaching comprises a step of putting the fluid for sustainedly activating the support into a broken state, with respect to the pipette tip having a support and a fluid enclosed therein in which the attachment opening is occluded by the perforable member or the detachable lid member or occluded by attaching the attachment opening to the connecting tube in which the perforable member is provided so as to intersect the axial direction of the attachment tube, and the opening is occluded by the detachable cap.

11. The method of treating the pipette tip having a support and a fluid enclosed therein according to claim 10, which further comprises a step of dissociating in which the material bonded to the support is dissociated from the support.

12. The method of treating the pipette tip having a support and a fluid enclosed therein according to claim 10, which further comprises:

a step of attaching a pipette tip to the nozzle after the pipette tip having a support and a fluid enclosed therein is detached from the nozzle, or before the pipette tip having a support and a fluid enclosed therein is attached to the nozzle;

a step of dispensing a liquid in which magnetic particles are suspended; and a step of applying magnetic field into the pipette tip from outside so that the magnetic particles are adsorbed on the inner wall of the pipette tip.

* * * * *